(12) United States Patent
Loubser

(10) Patent No.: US 6,901,928 B2
(45) Date of Patent: Jun. 7, 2005

(54) SUPERGLOTTIC AND PERI-LARYNGEAL APPARATUS FOR SUPRAGLOTTIC AIRWAY INSERTION

(76) Inventor: Paul G. Loubser, 302 Lakeglen Ct., Sugarland, TX (US) 77478

( * ) Notice: Subject to any disclaimer, the term of this patent is extended or adjusted under 35 U.S.C. 154(b) by 0 days.

(21) Appl. No.: 09/772,234

(22) Filed: Jan. 29, 2001

(65) Prior Publication Data

US 2001/0039949 A1 Nov. 15, 2001

Related U.S. Application Data

(63) Continuation-in-part of application No. 09/305,167, filed on May 4, 1999, now abandoned.

(51) Int. Cl.[7] .............................................. A61M 16/00
(52) U.S. Cl. ............................ 128/200.26; 128/207.14; 128/207.15
(58) Field of Search ................................. 600/239, 240; 128/200.26, 207.14, 207.15

(56) References Cited

U.S. PATENT DOCUMENTS

| | | | |
|---|---|---|---|
| 104,874 A | * 6/1870 | Osborn ......................... 452/70 |
| 412,409 A | * 10/1889 | Osborne ....................... 600/205 |
| 3,154,069 A | * 10/1964 | Ring ........................ 128/207.14 |
| 3,890,960 A | 6/1975 | nee Kuhn et al. | |
| 4,565,187 A | * 1/1986 | Soloway ....................... 600/193 |
| 4,697,578 A | * 10/1987 | Burgin ......................... 600/212 |
| 4,982,729 A | * 1/1991 | Wu ........................... 128/200.26 |
| 4,996,976 A | * 3/1991 | Nakagawa ..................... 362/572 |
| 5,003,963 A | * 4/1991 | Bullard et al. ........... 128/200.26 |
| 5,498,231 A | * 3/1996 | Franicevic ............... 128/200.26 |
| 5,590,643 A | 1/1997 | Flam | |
| 5,656,014 A | * 8/1997 | Rooney et al. .............. 600/240 |
| 5,743,254 A | * 4/1998 | Parker .................... 128/200.26 |
| 5,888,195 A | 3/1999 | Schneider | |
| 5,993,383 A | 11/1999 | Haase | |
| 6,003,510 A | 12/1999 | Anunta | |
| 6,053,166 A | * 4/2000 | Gomez ................... 128/200.26 |

* cited by examiner

*Primary Examiner*—Henry Bennett
*Assistant Examiner*—Mital Patel
(74) *Attorney, Agent, or Firm*—Pandiscio & Pandiscio

(57) ABSTRACT

A superglottic and peri-laryngeal apparatus for supraglottic airway device insertion that contemporaneously clears a patient's upper airway of the tongue and other pharyngeal tissues, and raises the epiglottis without use of the medical practitioner's fingers in the upper airway. The insertion apparatus comprises an offset member with a compressor-lever shield at a distal insertion end and a handle at the proximal end thereof. The offset member, medially disposed between the handle and the compressor-lever shield, should preferably be configured to be substantially flat, consistent in thickness throughout and having a tight, arcuate shape. The compressor-lever shield member preferably widens from its junction with the offset member into a broad tip at its leading distal edge.

11 Claims, 14 Drawing Sheets

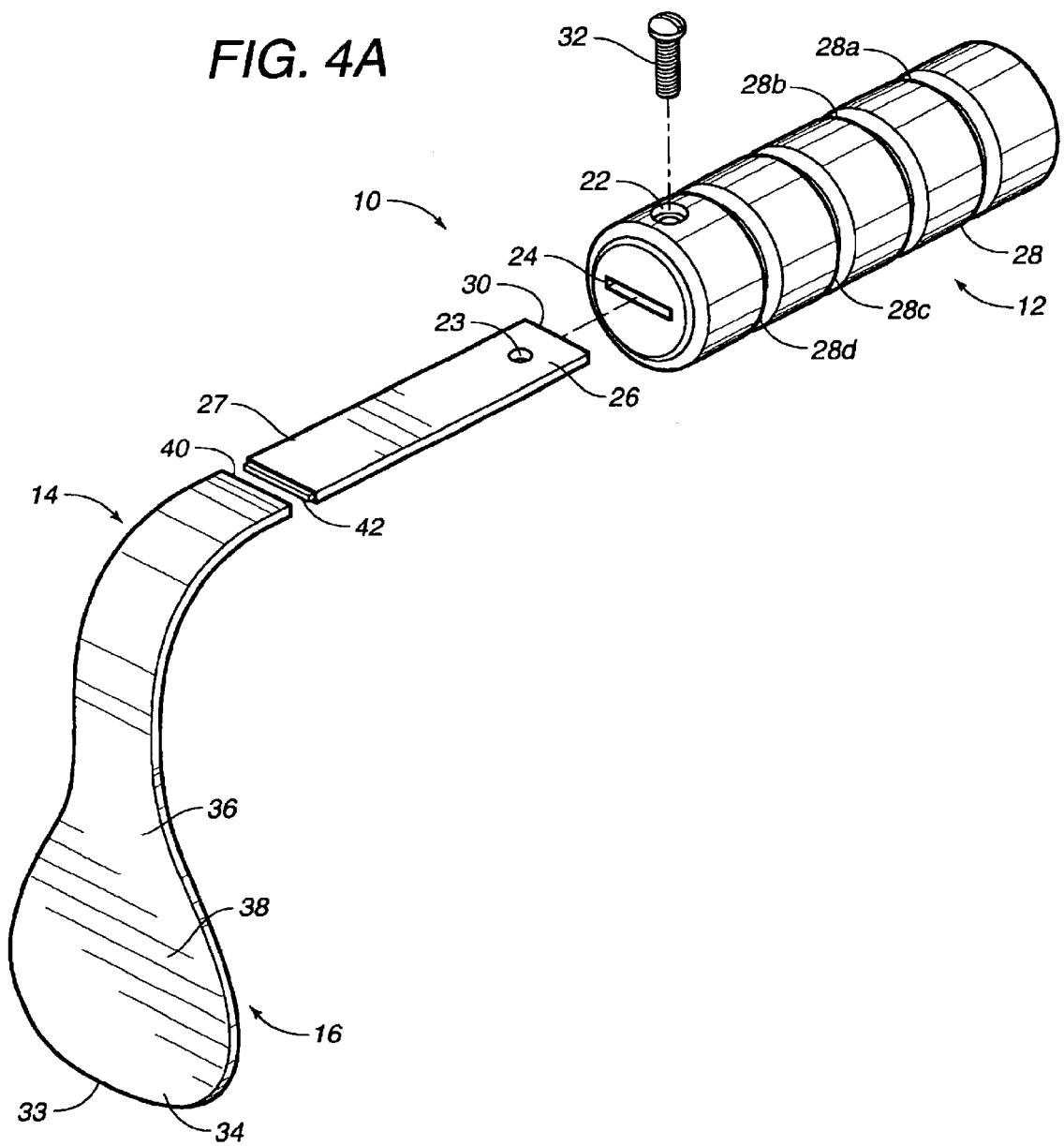

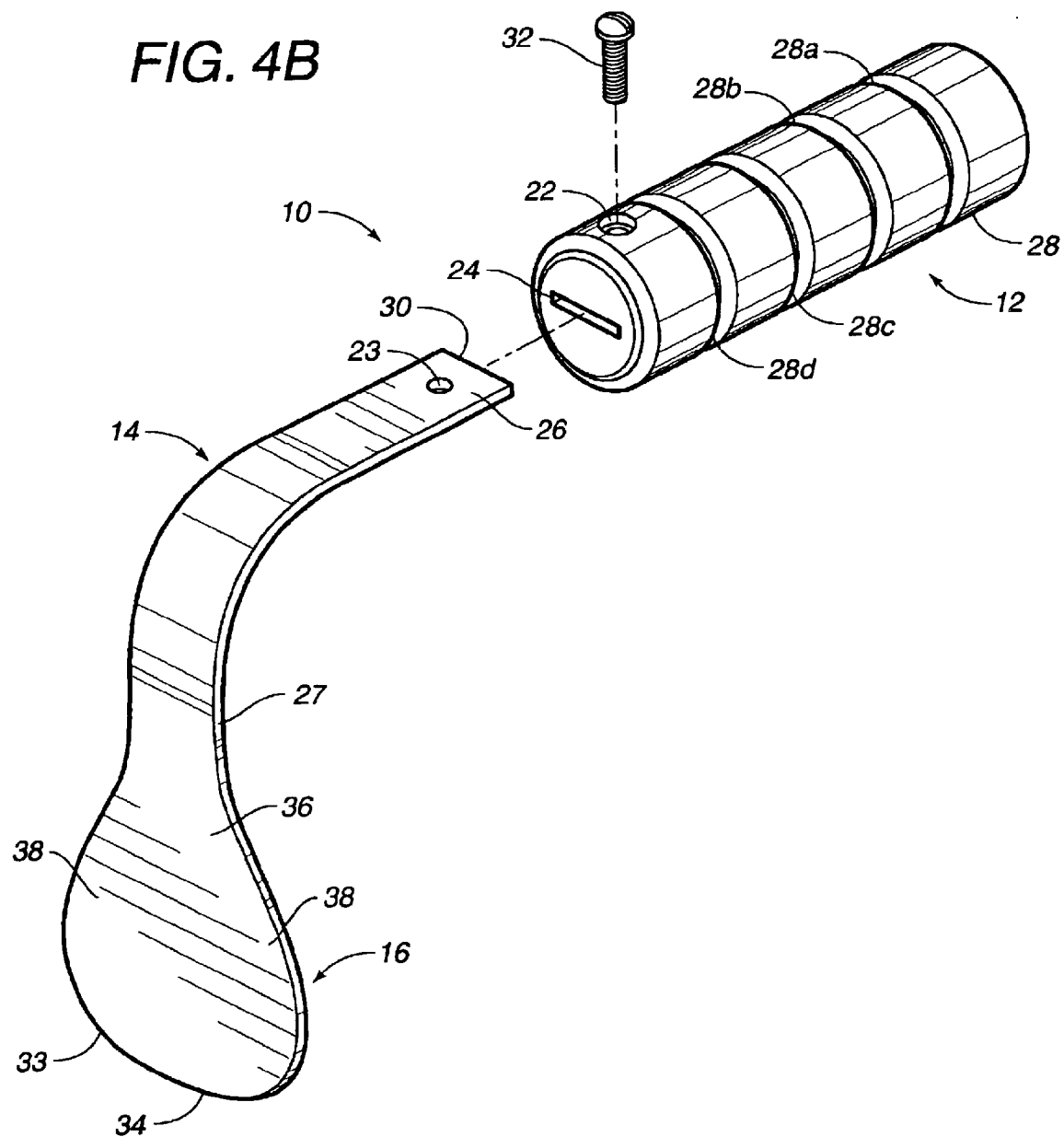

200

205

SUPERGLOTTIC AND PERI-LARYNGEAL APPARATUS FOR SUPRAGLOTTIC AIRWAY INSERTION

RELATED APPLICATIONS

This application is a continuation-in-part of U.S. application Ser. No. 09/305,167 filed May 4, 1999 ABN.

FIELD OF INVENTION

The present invention pertains to control of the human upper airway to facilitate insertion of airway maintenance devices for management of respiration, and, more particularly, pertains to superglottic and peri-laryngeal means and methods for optimizing the rapid, proper insertion of a laryngeal mask airway and other supraglottic airway devices into the supraglottic space disposed above the larynx.

BACKGROUND OF THE INVENTION

It is well known in the art that human airway management requires speed and efficiency. Successful insertion of an airway maintenance device into a patient must take place within 15–20 seconds to avoid hypoxia or even death. Before an airway maintenance device can be introduced into a patient, a medical practitioner must first complete certain preparatory airway control steps focused on clearing the patient's upper airway. For an unconscious patient, airway control includes clearing the tongue and other pharyngeal tissues that often obstruct the upper airway, both the buccal cavity in the mouth and the pharyngeal cavity in the throat.

It will be understood that the supraglottic region is the area of the pharynx including and immediately above the surface of the larynx where the base of the tongue meets the structures of the larynx. The laryngeal surface lies directly above the intersection between the trachea through which air passes into the lungs and the esophagus through which food passes into the stomach. The laryngeal surface includes the perilaryngeal tissues and cartilage of the vocal cords and the epiglottis. It is the epiglottis which regulates the flow of food into the esophagus and the flow of air into the larynx through the vocal cords and laryngeal inlet. The epiglottis is usually erect to allow the flow of air into the trachea during continuous breathing. When a person swallows, the epiglottis folds down to cover the larynx to protect the trachea and prevent aspiration of liquids and solids. For proper ventilation of a patient, the epiglottis must be erect and may be raised simply by tilting the patient's head or mechanically by applying pressure with a tool placed in the vallecula, a furrow between the epiglottis and the base of the tongue.

Supraglottic airway devices consist of air tubes attached to relatively large inflatable cuffs or pliant pads which seal above the larynx in the supraglottic region of the pharynx, either against the pharyngeal wall, such as the laryngeal mask airway, or "LMA," and the Cuffed Oropharyngeal Airway, or "COPA™." The GO2™ airway seals on the rim of the laryngeal inlet. When sealed, the supraglottic airways allow continuous flow of gases down the tube, through the larynx, and into the trachea. Because the airway device cuff or pad must be large enough to eventually seal by filling the open space in the throat, the cuffs and pads require more space for easy passage down the throat than do the air tubes to which they are attached. Since the cuffs and pads obscure the medical practitioner's line of sight into the pharyngeal cavity, the medical practitioner inserts these airway devices blindly, relying solely upon feel to avoid obstructions. For successful insertion of these airway devices, the airway device cuff or pad must not be obstructed by the tongue and other pharyngeal tissues as the airway device passes through the mouth and throat of the patient. It is crucial to prevent the cuff or pad from being caught on the epiglottis and folded down over the trachea, thereby blocking the flow of gases.

If the airway device cuff or pad is obstructed by the tongue or other pharyngeal tissues, the cuff or pad may lodge in the nasopharyngeal vault behind the soft palate because there is not enough space for the cuff or pad to make the turn around the bend of the throat. The inflatable cuff may even become folded back upon itself, or inside out, as it passes through the throat and then has to be removed and reinserted. Accordingly, the medical practitioner strives to synchronize the preparatory clearing of the tongue and other pharyngeal tissues and the insertion of the airway maintenance device, using one hand for clearing and the other for insertion, all the while feeling for and negotiating obstructions in the upper airway.

As will be appreciated by those skilled in the art, as a supraglottic airway device is pushed past these obstructions or lodges in the nasopharyngeal vault, tissue trauma results, frequently with bleeding. It is well known that patients often complain of a post-procedural sore throat. Unfortunately, there can also be rare but serious complications such as necrosis of the uvula, reduced flow of blood to the floor of the mouth, tongue paralysis and atrophy, and vocal cord paralysis.

As will be clear to those skilled in the art, a medical practitioner must also remove and reinsert an airway device in the case of epiglottic downfolding, where the airway device pushes the epiglottis down over the laryngeal inlet, thereby blocking the flow of air through the upper airway. This proclivity toward downfolding is a particular problem with the prevalent supraglottic device, the LMA, resulting in partial or complete obstruction of the upper airway and gastric insufflation. A further difficulty can occur if a downfolded epiglottis only partially blocks the airway, wherein distention of the stomach may be the first sign of trouble. To deal with such a situation, practitioners may need to interrupt active medical procedures to allow removal and reinsertion of the airway maintenance device. Removal and reinsertion of the inserted airway device considerably slows the airway control and maintenance procedures, particularly because the danger of hypoxia and organ damage or even death during the reinsertion of the airway device usually necessitates an intermediate pause for reoxygenation of the patient with the use of a simple face mask. Meanwhile, other medical procedures are delayed while the medical team waits for successful insertion of the LMA.

Accordingly, as will be clear to those skilled in the art, a tool used to contemporaneously clear the tongue and other pharyngeal tissues from the throat and mouth and raise the epiglottis would optimize rapid proper insertion of the LMA and other supraglottic airway devices thereby minimizing tissue trauma and post-procedural patient discomfort. Forceps have been used to pull the tongue forward to the front of the mouth, and tongue-depressors have been used to compress the tongue; however, neither forceps nor a tongue-depressor is effective for clearing the tongue and other pharyngeal tissues to create space in both the pharyngeal and buccal cavities, and neither can be used to raise the epiglottis. Forceps can slip and do not compress the entire surface of the tongue. Straight blade tongue depressors are not shaped to bend around the approximately 90° angle at the top of the throat and thus cannot flatten the surface of the tongue from its base all the way up and around through the buccal cavity. The tongue could obtrude beneath and around the depressor or slip back into the pharynx. A tongue-depressor could not contemporaneously approximate the vallecula to raise the epiglottis.

For example, Nakagawa, in U.S. Pat. No. 4,996,976, discloses a disposable straight-blade tongue depressor with an optical fiber light source. Inserted deep within the pharynx, Nakagawa could not follow the back surface of the tongue but would rest at an oblique angle to the tongue.

Curved tongue depressors are similarly limited. Osborne, U.S. Pat. No. 412,409 discloses a tongue-depressing insufflator similar to the mirrored depressor familiar from doctors and dentist' offices, wherein a small curved plate is used to gently depress the back curve of the tongue at the bend in the throat. The tongue is a fleshy, muscular organ with substantial depth beneath its surface; Osborne would be incapable of forcibly compressing, lifting, and flattening the entire tongue through the pharyngeal and buccal cavities.

In U.S. Pat. No. 3,890,960, Wunsch discloses a medical diagnostic inspection spatula having a slight, flat curve configuration, however the tool is configured with two prongs at the insertion end so that only the prongs rest on the base of the tongue. Wunsch is designed for examination of an awake patient without risk of triggering the gag reflex and could not be used compress the tongue out of the pharyngeal cavity or to raise the epiglottis.

Of course, many medical practitioners resort to manually lifting the tongue forward, but this requires putting one hand into the mouth of the patient where the hand itself obstructs insertion of the airway device. Furthermore, they cannot reach around the airway device to lift the epiglottis with their fingers.

This manual technique of clearing the tongue and other pharyngeal tissues, unfortunately, places both the medical practitioner and patient at heightened risk of infection, allergic reaction, and injury. Indeed, such a manual technique creates a risk of contamination and disease for both practitioner and patient: the medical practitioner's gloved hand may introduce latex glove powder and germs into the patient's mouth; the patient's teeth and any orthodontic devices may damage the medical practitioner's glove and hand.

Practitioners in the art are conversant with laryngoscopes as airway control tools that allow a practitioner to visualize the vocal cords and raise the epiglottis for endotracheal intubation, wherein a thin tube is passed through the larynx and directly into the trachea below. However, as is known in the art, these laryngoscopic blades do not create space for the supraglottic devices which stop above the larynx. The blades merely displace the tongue sideways out of the line of sight of the medical practitioner; the blades do not compress the tongue out of the pharyngeal cavity or flatten the tongue in the buccal cavity. Laryngoscopic blades have been developed in two general types: straight blades and curved blades having a curvature greater than the curvature of the pharynx. Both types of blades would obstruct the insertion of the cuffs or pads and attached tubes of supraglottic airway devices.

For example, Schneider, in U.S. Pat. No. 5,888,195, teaches a blade which allows better visualization of the larynx by providing a adjustable curvature. Nevertheless, this blade fails to compress and coax the tongue out of the pharynx or flatten the tongue in the buccal cavity.

Haase, in U.S. Pat. No. 5,993,383, discloses a laryngoscopic blade that purports to improve tongue control during intubation, using wing sections to compress the tongue out of the line of sight.

In addition to laryngoscopic blades, there are other devices which are purported to control the tongue during anesthesia. For control of the tongue in the awake or mildly sedated as well as the unconscious patient, Flam, in U.S. Pat. No. 5,590,643 discloses an oral intubating airway with a bite block designed to keep a patient's mouth open for insertion of various medical instruments. A short C-shaped tongue retractor is attached to the bite block to hold part of the tongue forward in the mouth and out of the throat. The retractor is short to avoid triggering the gag response.

Anunta, in U.S. Pat. No. 6,003,510, tangentially addresses the problem of flattening the tongue in the buccal cavity, but not the pharyngeal cavity. Anunta discloses a thin flat tool configured with a flattened curve which is inserted after the LMA is introduced into the buccal cavity to leverage the LMA away from the posterior wall of the pharynx so that the LMA cuff does not fold back upon itself. Anunta has an optional, ancillary use to first compress the tongue within the buccal cavity before introduction of the LMA into the buccal cavity. Anunta is designed expressly for use in the buccal cavity and could not be used to clear the upper airway by compressing the tongue and raising the epiglottis.

Thus, it is clear that there is presently no device or procedure for optimizing blind insertion of a supraglottic airway device in a patient. It would be advantageous to utilize an apparatus that enables space to be created for passage of such an airway device and attached cuff or pad by compressing and coaxing the tongue upwards and forwards to the front of the mouth. Accordingly, these limitations and disadvantages of the prior art are overcome with the present invention, and improved means and techniques are provided that are useful for increasing space in the pharyngeal cavity while simultaneously flattening the tongue in the mouth, whereby space in the buccal cavity is increased. The present invention also contemplates a tool configured with a tip wide enough to approximate the vallecula and to raise the epiglottis, and to be easily removable without disturbing the position of the cuff or pad or attached air tube of a superglottic airway device, to avoid interfering with the rapid sealing of the device in the pharynx or on the larynx per se.

SUMMARY OF THE INVENTION

The present invention comprises a superglottic and peri-laryngeal apparatus for supraglottic airway device insertion. As will be hereinafter described in detail, the insertion apparatus of the present invention contemporaneously clears the patient's upper airway of the tongue and other pharyngeal tissues, and raises the epiglottis without use of the medical practitioner's fingers in the upper airway. In so doing, embodiments of the present invention enable insertion of supraglottic airway devices with virtually no wasted motion and minimal obstruction, thereby minimizing tissue trauma and complications, particularly those resulting from time-consuming re-introductions of an airway device.

The preferred embodiment of the insertion apparatus comprises an offset member with a compressor-lever shield at a distal insertion end and a handle at the proximal end thereof, as will be described hereinafter in detail. The offset member, medially disposed between the handle and the compressor-lever shield, should preferably be configured to be substantially flat, consistent in thickness throughout and having a tight, arcuate shape. As will be appreciated by practitioners in the art, the proximal end of the offset member may include a marker to guide the practitioner in determining when the insertion aid has been fully advanced into the patient's supraglottic region.

The compressor-lever shield member of the present invention preferably widens from its junction with the offset member into a broad tip at its leading distal edge. The perimeter edge of the compressor-lever shield is preferably comprised of a buffered safety edge to prevent tissue trauma as the compressor-lever shield is being advanced through the patient's pharyngeal cavity and, ultimately, into the vallecula. The compressor-lever shield should preferably be constructed in a flat configuration, but alternatively may be constructed in a concave configuration in order to achieve the guiding function contemplated by the present invention, wherein the insertion of an airway device into the supraglottic region of the patient's upper airway is conveniently and safely effectuated.

As will be understood by those skilled in the art, the handle member preferably provides a slip-resistant grip to stabilize a medical practitioner's finger position while an insertion apparatus is held and manipulated. Additionally, it will be appreciated that the proximal end of the offset member may include a marker band to guide the practitioner in determining when the insertion apparatus has been fully advanced into the patient's supraglottal region.

The preferred embodiment of the insertion apparatus comprises an integral construction with the handle member, offset member, and compressor-lever shield member fixedly interconnected as an entire unit. Alternatively, embodiments of the insertion apparatus may be configured as an assembly having separable component members that are assembled and disassembled, as appropriate. Embodiments of the insertion apparatus should preferably be constructed of stainless steel for compatibility with conventional sterilization methods and for reuse. It will be understood, however, that embodiments may be constructed of any suitable sterilizable materials known in the art. Of course, disposable embodiments may be constructed of sufficiently strong plastic or other suitable materials known in the art.

It is contemplated by the present invention that, for each patient, a practitioner will select an appropriate embodiment of the insertion apparatus from among several series sized and shaped to suit the size and associated conformation of adult and pediatric upper airways. It will be appreciated that, by using an assembly configuration of the present invention, a medical practitioner may be able to specifically match the size and shape of the offset member and the compressor-level shield of the present invention to the anatomical features of a patient's upper airway.

Generally, to use the present invention, a medical practitioner adjusts the patient's head and neck into the proper position for insertion of a supraglottic device. With the left hand, the practitioner then inserts the present invention into the open mouth of the patient, above the tongue. The apparatus is then rotated anteriorly to advance around the tongue and through the pharyngeal cavity until the leading distal edge of the compressor-lever shield rests in the vallecula. Gentle application of forward and anterior traction from the base of the tongue compresses and lifts the tongue forward and simultaneously lifts the epiglottis. Finally, while continuing to exert gentle traction with one hand, the practitioner uses the other hand to insert the supraglottic airway device posterior to the insertion apparatus.

It will become evident that use of the present invention in this manner increases the space in the pharyngeal cavity, enhances access to the laryngeal inlet, and assures an open airway. Having thus made adequate space in the buccal and pharyngeal cavities of the patient, the medical practitioner can freely and rapidly insert the airway device without tissue trauma and complications. It will be understood that the airway device does not become impacted in the nasopharyngeal vault but, due to the functionality enabled by embodiments of the present invention, can bend around the back of the throat and pass on through the pharyngeal cavity to the hypopharynx. The airway device is, accordingly, prevented from catching and downfolding the tip of the epiglottis and thereby occluding the upper airway. It should thus be apparent that the teachings of the present invention improve the manner and means for inserting an LMA and other supraglottic airway devices.

It is accordingly an object of the present invention to provide a superglottic and peri-laryngeal insertion apparatus for facilitating the insertion of an LMA and other supraglottic airway devices in a patient.

It is another object of the present invention to provide a superglottic and perilaryngeal insertion apparatus for in specially sized and shaped series for the adult, pediatric and premature upper airways.

It is yet another object of the present invention to provide a superglottic and peri-laryngeal insertion apparatus for reducing or eliminating postoperative complications due to improper insertion of an LMA and other supraglottic airway devices.

It is still another object of the present invention is to provide a convenient method for assuring proper insertion of an LMA and other supraglottic airway devices.

It is still another object of the present invention is to provide a kit for aiding the insertion of an LMA and other supraglottic airway devices, wherein such a kit comprises the insertion apparatus of the present invention preferably contained in a sterilized or sterilizable package.

These and other objects and features of the present invention will become apparent from the following detailed description, wherein reference is made to the figures in the accompanying drawings.

IN THE DRAWINGS

FIG. 4A depicts a frontal perspective view of an embodiment of the insertion apparatus of the present invention constructed with a full assembly configuration.

FIG. 4B depicts a frontal perspective view of an embodiment of the insertion apparatus of the present invention constructed with a partial assembly configuration.

DETAILED DESCRIPTION OF THE INVENTION

The present invention provides an optimal tool for creating sufficient space for passage of a supraglottic airway device and attached cuff or pad into a patient's upper airway. As will be evident to those skilled in the art, by compressing and coaxing the tongue upwards and forwards to the front of the mouth, embodiments of the present invention increase space in the pharyngeal cavity while simultaneously flattening the tongue in the mouth, thereby increasing space in the buccal cavity. Such an optimal tool inherently raises the epiglottis into the bowl of the descended airway device cuff or pad, and is easily removable from a patient's mouth without disturbing the position of the cuff or pad or the attached airway tube, so as not to interfere with the rapid sealing of the airway device in the pharynx or on the larynx, per se. As will be clear to those skilled in the art, this optimal tool provided by the present invention reduces the risk of hypoxia, death, and other serious complications.

Figure 1:
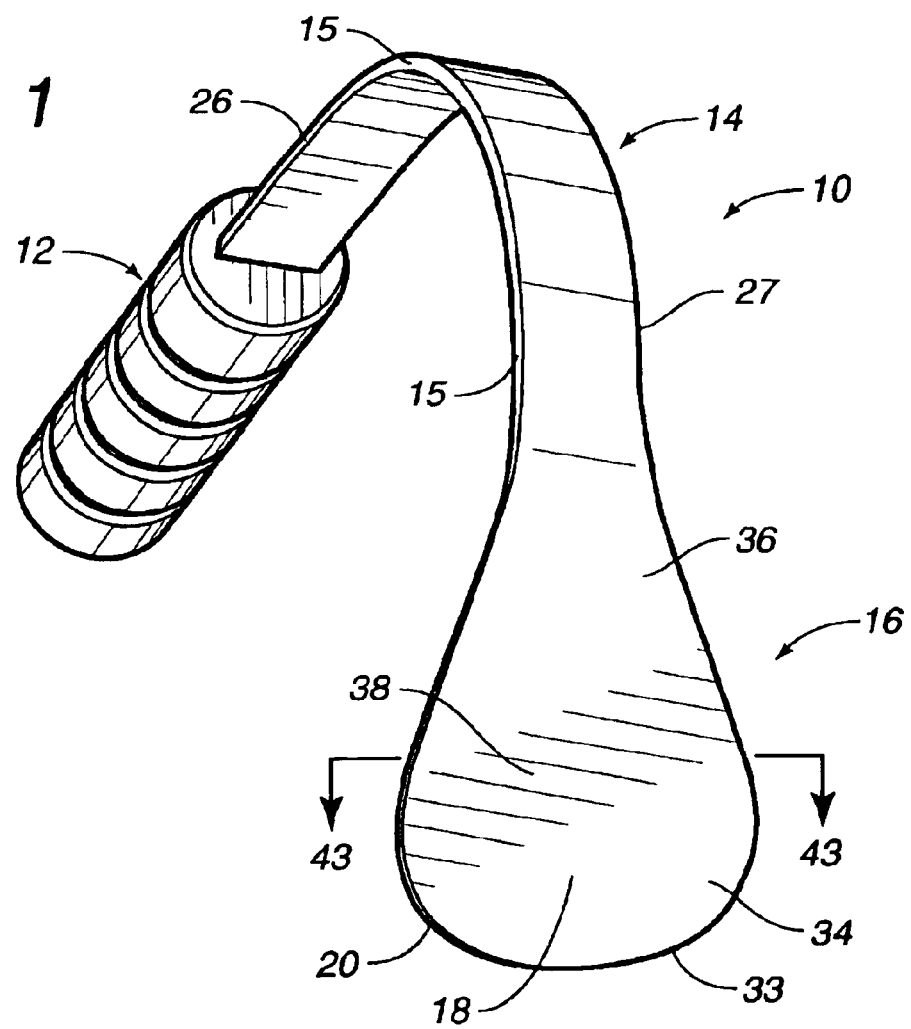
FIG. 1 is a perspective view of the preferred embodiment of the superglottic and peri-laryngeal insertion apparatus for supraglottic airway devices.
Figure 2:
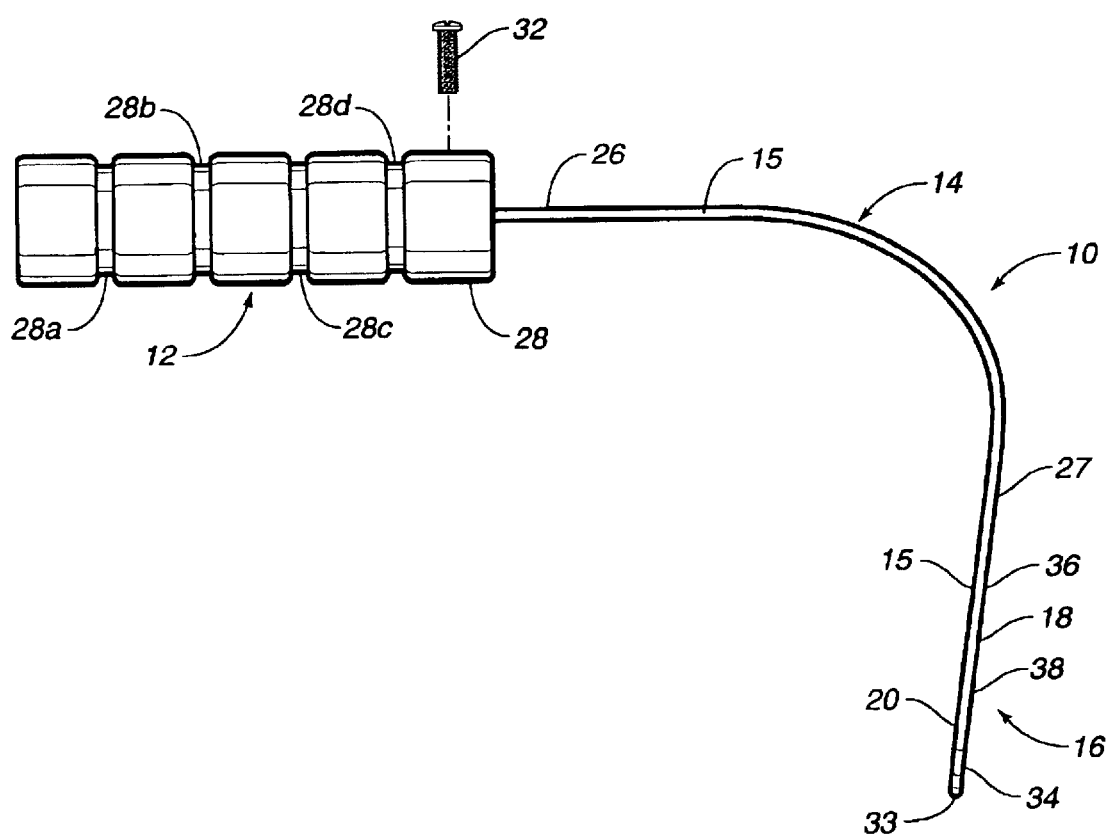
FIG. 2 is a perspective side view of the preferred embodiment depicted in FIG. 1.

Referring now to the drawings, FIGS. 1 and 2 illustrate the preferred embodiment of superglottic and peri-laryngeal insertion apparatus 10. Insertion apparatus 10 comprises handle member 12, offset member 14, and compressor-lever shield member 16. Proximal end 26 of offset member 14 is interconnected with handle member 12, and distal end 27 of offset member 14 is interconnected with compressor-lever shield 16. The insertion apparatus of the present invention is preferably contained in a sterilized or sterilizable package for ready, safe use by the practitioner. The insertion apparatus per se is preferably constructed as reusable from readily sterilizable materials of sufficient strength known to those skilled in the art. These materials may render the apparatus either rigid or slightly flexible so that it yields slightly with the application of forward and anterior traction. The insertion apparatus may alternatively be made of disposable materials known to those skilled in the art.

In the preferred embodiment, handle member 12 has a cylindrical shape including slip-resistant grip 28 to stabilize the finger position of the medical practitioner while holding and manipulating the insertion apparatus 10. In the preferred embodiment, positive grip 28 comprises a plurality of groove means 28a, 28b, 28c, 28d disposed approximately a finger-width apart along the length of handle member 12. It will be clear, however, that the handle may be constructed in any shape which provides the practitioner a suitable and comfortable grip, including, for example, a series of alternating ridges and valleys disposed along the handle or a single medial bulge to stabilize the grip of the palm.

Offset member 14 is preferably flat having an edge 15 with thickness substantially constant in height throughout, and configured with an arcuate shape. It will be understood that this offset member is preferably shaped like a curved letter "L," rounded at the angular bend between the generally straight pair of legs thereof. It has been found that such a configuration readily accommodates the shape of the human upper airway.

The present invention contemplates that a medical practitioner in the art will select an embodiment of the insertion apparatus to suit the general anatomical features of a patient's upper airway. It will thus be evident that a relatively large embodiment thereof will be used to accommodate a large adult, with progressively smaller embodiments used to accommodate the upper airways of medium and small adults or adolescents. It has been found that a separate pediatric series of embodiments are preferable to accommodate large, medium and small children, with a miniature size to accommodate premature babies. Thus, a practitioner in the art will be able to choose a suitable offset member on the basis of the length of the offset member's legs and the angle of the bend therebetween, in order to accommodate the size and conformation of a patient's head and neck.

The Adult series of offset member 14 constitutes several sub-series wherefrom a practitioner may accommodate the conformation of a patient's upper airway. The practioner usually selects from among the Large, Medium, and Narrow sub-series on the basis of a patient' weight. The appropriate weight ranges that have been found to be useful for selecting an approximately sized embodiment are:

Large Adult Series: Males ≧90 kg.

Medium Adult Series: Males ≦90 kg. and Females ≧60 kg.

Small Adult Series: Females ≦60 kg.

It should be evident that selection of an appropriate pediatric series would be similar.

Having selected a sub-series based on overall size of the patient, the practitioner then selects from within that series on the basis of the offset member spread. That is, the offset member spread corresponds to the distance between the proximal end 26 and the distal end 27 of the offset member 14. Thus, it will be understood that the medical practitioner should preferably judge the conformation of the patient's upper airway to determine the length of the offset member leg and the angle of the offset member bend that will best fit the length of the patient's buccal and pharyngeal cavities, and the angle of the bend around the surface of the tongue.

It will be clear to those skilled in the art that the offset member preferably should not constitute such excess length as to reach too far down the pharyngeal cavity of the patient and consequently damage the structures of the larynx. Similarly, the offset member preferably should not extend too far out of the patient's mouth to thereby fail to provide the practitioner sufficient leverage to compress and lift the tongue. Likewise, the offset member should not constitute such insufficient length so as not to reach the base of the tongue and the vallecula, or to end within the buccal cavity wherein the patient's teeth abut the handle of the insertion apparatus.

Similarly, the medical practitioner should preferably select from within the appropriate sub-series so that the bend in the offset member accommodates the conformation of the bend at the top of the patient's throat. This procedure, of course, tends to assure that the insertion apparatus comes into flush contact with the surface of the patient's tongue, thereby allowing the medical practitioner to compress and lift the tongue in the pharyngeal cavity while simultaneously flattening it in the buccal cavity. It will be appreciated that embodiments of the insertion apparatus may not be able to fulfill this function if the angle is too large for the conformation of the upper airway, resulting in a gap between the offset member and the surface of the tongue. Such a gap could damage the pharyngeal and/or buccal tissues or structures if the angle is too small for the conformation of the patient's upper airway. More particularly, Table I enumerates offset member size ranges applicable to variously sized adults:

TABLE I

| | | ADULT LENGTH OF LEG | | ADULT ANGLE OF BEND |
|---|---|---|---|---|
| ADULT OFFSET MEMBER SPREAD End-to-End | | Proximal Side (Inches) | Distal Side | Range (Degrees) |
| Large | Broad | 4.0–6.0 | 4.0–6.0 | 45–110 |
| | Preferred | 4.0–5.5 | 4.0–5.5 | 80–90 |
| | Narrow | 4.5–5.5 | 4.5–5.5 | 75–85 |
| Medium | Broad | 3.0–5.0 | 3.0–5.0 | 45–110 |
| | Preferred | 3.0–4.5 | 3.0–4.5 | 80–90 |
| | Narrow | 3.5–4.5 | 3.5–4.5 | 75–85 |
| Small | Broad | 2.0–4.0 | 2.0–4.0 | 45–110 |
| | Preferred | 2.0–3.5 | 2.0–3.5 | 80–90 |
| | Narrow | 2.5–3.5 | 2.5–3.5 | 75–85 |

Similarly, Table II enumerates offset member size ranges applicable to variously sized children:

TABLE II

| PEDIATRIC OFFSET MEMBER SPREAD End-to-End | | PEDIATRIC LENGTH OF LEG | | PEDIATRIC ANGLE OF BEND |
|---|---|---|---|---|
| | | Proximal Side (Inches) | Distal Side | Range (Degrees) |
| Large | Broad | 1.5–3.0 | 1.5–3.0 | 45–110 |
| | Preferred | 2.0–3.0 | 2.0–3.0 | 80–90 |
| | Narrow | 2.0–2.5 | 2.0–2.5 | 75–85 |
| Medium | Broad | 1.0–2.5 | 1.0–2.5 | 45–110 |
| | Preferred | 1.5–2.5 | 1.5–2.5 | 80–90 |
| | Narrow | 1.5–2.0 | 1.5–2.0 | 75–85 |
| Small | Broad | 0.75–2.0 | 0.75–2.0 | 45–110 |
| | Preferred | 1.0–2.0 | 1.0–2.0 | 80–90 |
| | Narrow | 1.0–1.5 | 1.0–1.5 | 75–85 |

| PEDIATRIC MINI (PREMATURE INFANT) OFFSET MEMBER SPREAD End-to-End | PEDIATRIC MINI (PREMATURE INFANT) LENGTH OF LEG | | PEDIATRIC MINI (PREMATURE INFANT) ANGLE OF BEND Range (Degrees) |
|---|---|---|---|
| | Proximal Side (Inches) | Distal Side | |
| Broad | 0.5–1.5 | 0.5–1.5 | 45–110 |
| Preferred | 0.5–1.25 | 0.5–1.25 | 80–90 |
| Narrow | 0.5–1.0 | 0.5–1.0 | 75–85 |

For example, referring to Table I, presented with a male patient having weight less than 90 kg., the practitioner will usually select from the Medium sub-series of the insertion apparatus. Then, with or without the aid of x-rays of the head and neck of the patient, the practitioner chooses a Broad, Preferred, or Narrow sub-series of offset member. For the purposes of this example, if the Preferred Spread is chosen for the patient, the practitioner then has additional choice of a combination of leg lengths and angles and may choose, say the offset member having a distal and proximal leg length of 3.0 inches, bending at an angle of 90°. A practitioner would select from the Pediatric series enumerated in Table II in a similar manner.

Those skilled in the art will appreciate that, although the angle of the bend in the offset member is represented by a series of ranges in Tables I and II, the largest and smallest angles contemplated by the present invention are about 110° and about 45°, respectively. The insertion apparatus of the present invention thus conforms to what may be regarded as a strongly arcuate shape. It has been found that flattened or broad curves tend to inhibit the purposes of the present invention. It will also be noted by those skilled in the art that the Adult and Pediatric series contemplate consistent ranges of angles, such that the Broad Spread offset members comprise a range of about 45° to about 110°, the Preferred Spread offset members comprise a narrower range of about 80° to about 90°, and the Narrow Spread comprise a narrow range of about 75° to about 85°.

Turning now to the general formation of the offset member, the preferred embodiment of the present invention comprises a consistent width throughout. It has been found that the preferred width may range from about 1.0–2.0 cm. for adult sizes and from about 0.5–1.0 cm. for pediatric sizes. However, it is also contemplated by the present invention that in any one embodiment, the width may vary along the length of the offset member. For example, as shown in Table I, an alternative embodiment of the Large Adult series may comprise an offset member relatively wide along the proximal side which narrows at the distal side. Thus, a Broad embodiment in the Large Series would comprise a 2.0 cm. wide proximal side of offset member 14 near the handle 12 and a 1.0 cm. wide distal side of the offset member near shield 16. Such variations in width, of course, allow for differing conformations of the human upper airway.

Likewise, although edge 15 is preferably constructed with a height consistent in thickness throughout for any one embodiment of offset member 14, the height may vary in thickness from embodiment to embodiment. Accordingly, it will be clear that the offset member may be constructed in any thickness which provides the practitioner with an insertion apparatus embodiment of appropriate strength, stability and suitability to the conformation of a patient's upper airway. This range of thicknesses has generally been found to vary between about 1–3 mms.

It has been found to be advantageous that embodiments of the present invention include a marker means disposed at the proximal end 26 of the offset member 14 to guide the medical practitioner ascertain when the insertion apparatus 10 has been fully advanced into the patient's superglottic region. For instance, such a marker means may comprise a notch, a band, a ridge, or some other visual indication. Brightly colored markers—yellow or chartreuse are particularly conspicuous—appear to facilitate easy visualization by medical practitioners.

Figure 3A:
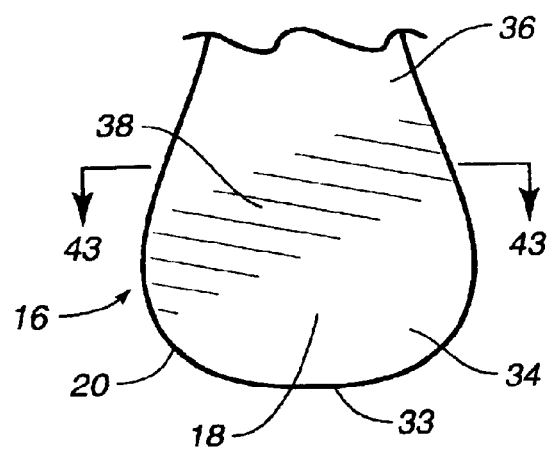
FIG. 3A is an exploded view of the compressor-lever shield member of the embodiment depicted in FIGS. 1 and 2.

Referring now to FIGS. 1, 2 and 3A, compressor-lever shield member 16 connects with the distal end 27 of offset member 14. In the preferred embodiment, the compressor-lever shield is constructed of consistent thickness with the offset member; in alternative embodiments, the compressor-lever shield may have variable thickness as is appropriate to accomplish the purposes of the present invention. Compressor-lever shield member 16 comprises three sections: front insertion-end section 34, back section 36, and middle section 38 disposed between the front and back sections. In addition, shield member 16 is configured with upper surface 18, lower surface 20, and perimeter edge member 33.

Lower surface 20 constitutes the surface of the shield member which lies against the patient's tongue at the anterior side of the pharynx for enabling the gentle application of forward and anterior traction from the base of the tongue upwards. Upper surface 18 constitutes the surface of the shield which is in contact with the supraglottic airway device towards the posterior side of the pharynx. Accordingly, the upper surface of the shield member of the present invention functions as an interface between a supraglottic airway device and the patient's tongue.

Figure 3B:
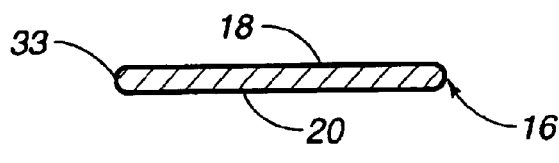
FIG. 3B depicts a cross-sectional view along line 43—43 of the flat shield member depicted in FIG. 3A.
Figure 3C:
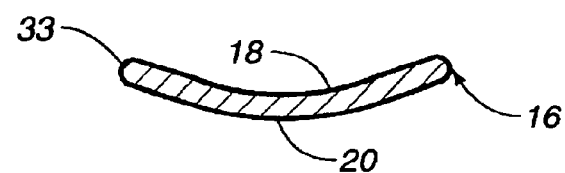
FIG. 3C depicts a cross-sectional view along Line 43—43 of an alternative, concave embodiment of the shield member of the present invention depicted in FIG. 3A.

As seen in the cross-sectional view depicted in FIG. 3B, shield member 16 should preferably be constructed in a flat configuration. Alternatively, as shown in FIG. 3C, the shield member may be curved, forming a channel along the shield's longitudinal axis. It will be appreciated that this alternate embodiment may be preferable for guiding the insertion of certain supraglottic airway devices that seal within the rim of the laryngeal inlet rather than against the pharyngeal structures of the supraglottic region. In this alternate embodiment, upper surface 18 would be concave and lower surface 20 correspondingly convex.

Referring now to FIGS. 1 and 3A, perimeter edge 33 of the shield member preferably widens along back section 36 and middle section 38, curving distally from its junction with the offset member to the front insertion end. Middle section 38 is preferably the widest part of the shield member. However, the compressor-lever shield of the present invention is not limited in shape to the embodiment seen in FIGS. 1 and 3A. The present invention contemplates that the shield member may be of any shape and size that would allow compression and lift of the tongue and that would also provide a broad enough tip for the leading distal edge of the shield to advance into the vallecula and lift the epiglottis, as herein described in detail. It has been found that at its widest point, the compressor-lever shield should preferably comprise a width approximately twice the width of the proximal and distal arms of the offset member, or generally within a range of 2–3 times the offset member width, with an optimal range of 2–2.5 times the offset member width. It should be clear that the shape and dimensions of the compressor-lever shield should ideally match—conform to—the size and configuration of a patient's supraglottic region of the upper airway.

It is clearly seen that, in the preferred embodiment in FIGS. 1 and 2, perimeter edge 33 curves gently outwards at middle section 38. In an alternative embodiment, middle section 38 may be substantially wider so that perimeter edge 33 flares out broadly. In yet another embodiment, sections 36, 38, and 34 may widen distally from offset member 14 with perimeter edge 33 curving only at front section 34 to round the tip of the distal insertion end. Of course, the compressor-lever shield of the present invention is not limited to these embodiments but may be of any size and shape suitable to the purposes described herein. The present invention contemplates the construction of the insertion apparatus in adult and pediatric series so that a practitioner will choose a suitable compressor-lever shield for each patient.

Perimeter edge 33 of the compressor-lever shield member should preferably be constructed with a buffered safety edge to prevent tissue trauma as the compressor-lever shield is being advanced through the patient's pharyngeal cavity and then proceeds into the vallecula. Such safety edge is preferably comprised of a smooth and rounded rim, but is not limited to any one form. Accordingly, this safety edge may comprise a beveled edge, a bull-nose rim, or other suitable edge construction known in the art. In other embodiments, the safety edge may alternatively comprise padded or flexible material or some other safety-edge means that will yield slightly simultaneously when the instant insertion apparatus is pressed along the tongue and other structures of the pharynx. It should be evident that such safety edge means will protect against the remote possibility of tissue trauma being caused by robust insertion of the present invention.

Referring now to FIGS. 1, 2 and 4A, insertion apparatus 10 of the present invention may be integrally constructed with handle member 12, offset member 14, and compressor-lever shield member 16 integrally connected as one entire unit as seen in FIGS. 1 and 2. Alternatively, the insertion apparatus may be configured as an assembly with separate component members which are to be assembled and disassembled. FIG. 4A shows an assembly configuration of insertion apparatus 10, comprising separate handle member 12, separate offset member 14, and separate compressor-lever shield member 16. Such assembly configuration provides the medical practitioner maximum flexibility to specifically match the sizes and shapes of offset member 14 and compressor-level shield member 16 with the anatomical features of a patient's upper airway.

Figure 4C:
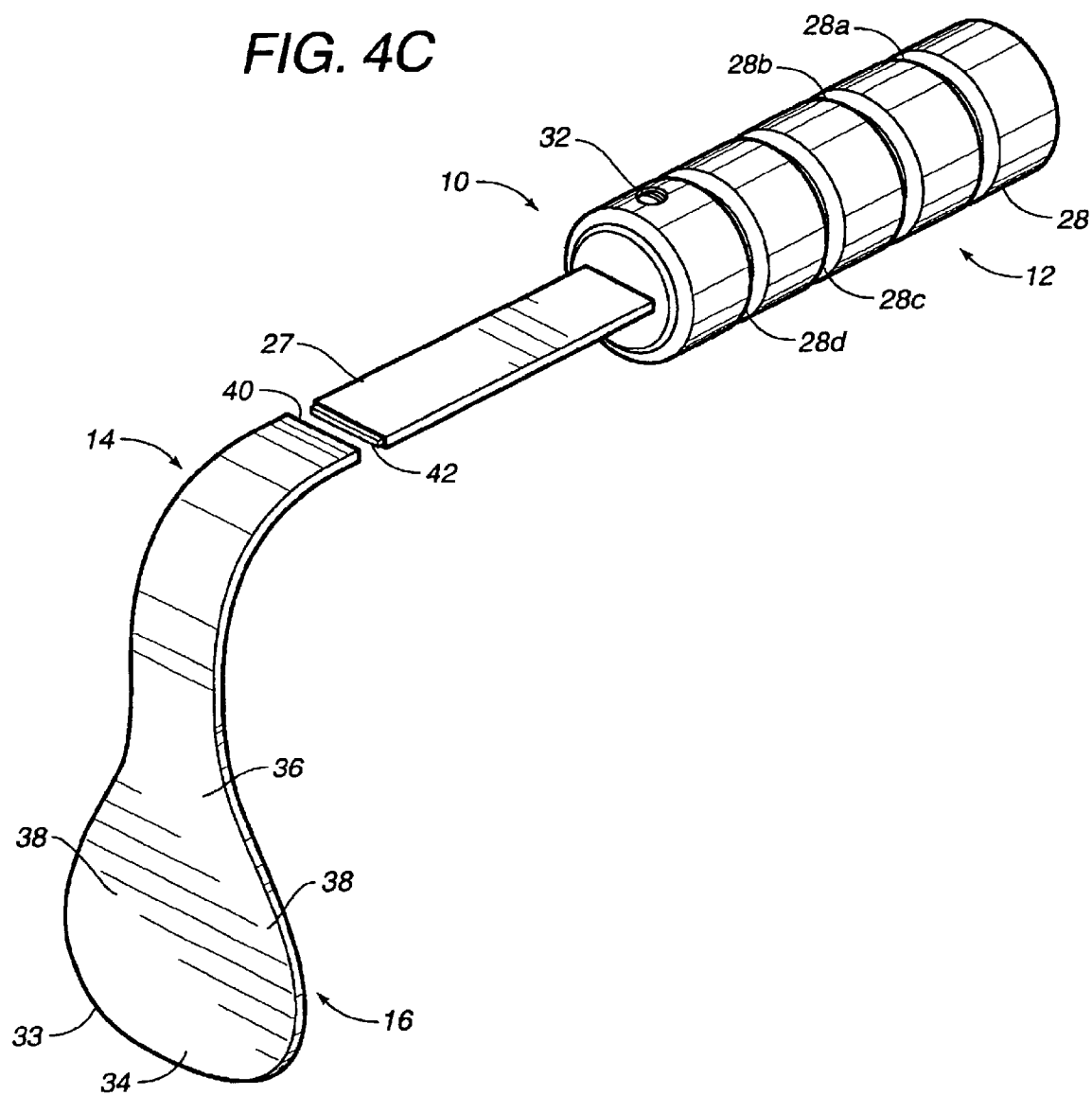
FIG. 4C depicts a frontal perspective view of another embodiment of the insertion apparatus of the present invention constructed with a partial assembly configuration.

Other alternatively configured embodiments include partial assemblies; two illustrative embodiments of which are seen in FIGS. 4B, and 4C. FIG. 4B shows an embodiment wherein separate handle member 12 is adapted to be assembled with an integral offset member 14 and compressor-lever shield member 16. FIG. 4C shows another illustrative partial assembly embodiment wherein separate compressor-shield member 16 is adapted to be assembled with integral handle member 12 and offset member 14.

It will be evident that such assembly and partial assembly embodiments allow a diverse mix of suitable readily sterilizable and disposable components known in the art. For example, an embodiment might constitute an assembly of reusable sterilizable stainless steel handle with a disposable offset member and disposable compressor-lever shield member. Furthermore, offset member 14 may comprise a metal or other suitable material known in the art, such as heat-susceptible plastic, that may be bent to adjust the angle of the offset member for use with a particular patient. It is also within the teachings of the present invention to contain and deliver the individual component members of the insertion apparatus in a sterilized or sterilizable package.

Referring again to FIG. 4A showing an insertion apparatus constructed as an assembly, every embodiment of the present invention comprising offset member 14 having a proximal end 26 and a distal end 27. The offset member has an attachment means 30 disposed at its proximal end 26 for connection with handle member 12. The offset member also has an attachment means 42 at its distal end 27 for connection with the compressor-lever shield member. Handle member 12 has connector means 24 for receiving and holding the proximal end of the offset member; and the compressor-lever shield 16 has connector means 40 for receiving and holding the distal end of the offset member.

FIG. 4A depicts an embodiment wherein both the handle and compressor-lever shield members are attached to the offset member by a tongue and groove connection means. Specifically, in this embodiment, both handle connector means 24 and shield connector means 40 comprise slotted channels with detent means for receiving and holding the correspondingly notched tongue means of the offset member. Thus, in this embodiment, attachment means 30 at proximal end 26 of the offset member comprises a notched tongue means which slides into slotted channel 24 in handle 12, and attachment means 42 at distal end 27 of the offset member is a corresponding notched tongue means which slides into slotted channel 40 of shield 16. The detent means positioned within each slotted channel engage the notched tongue means to secure the offset member. Because of the torque applied to the handle as the insertion apparatus is rotated to apply forward and anterior traction to compress and lift the tongue and raise the epiglottis, offset member tongue attachment means 30 is retained within handle slot means 24 by action of a set screw 32 or the like preferably threaded through hole 22 into corresponding hole 23 in offset member tongue means 30.

FIG. 4B shows an alternative partial assembly embodiment wherein compressor-lever shield 16 and offset member 14 are integrally connected and handle 12 is separately attachable by the tongue and groove connection means hereinbefore described. FIG. 4C shows an alternative embodiment wherein separately attachable compressor-lever shield 16 is to be assembled with integrally connected handle member 12 and offset member 14. It is clear that the shield member attaches with a tongue and groove connection means.

Of course, it will be understood that alternate means of connecting the insertion apparatus component members are well known in the art and are contemplated within the scope of the present invention. Tongue and groove connection means are well suited to the flat and relatively thin construction of the offset member and compression-lever shield. With no need for screws or latches along the length of the portion of the apparatus which enters the patient's mouth, there is less chance of tissue trauma. However, the present invention contemplates any alternative embodiments wherein component members may be separately attached by suitable connection means. For example, handle member 12 could be separately attachable to offset member 14 by a threaded bolt and channel connection means.

Figures 5A, 5B:
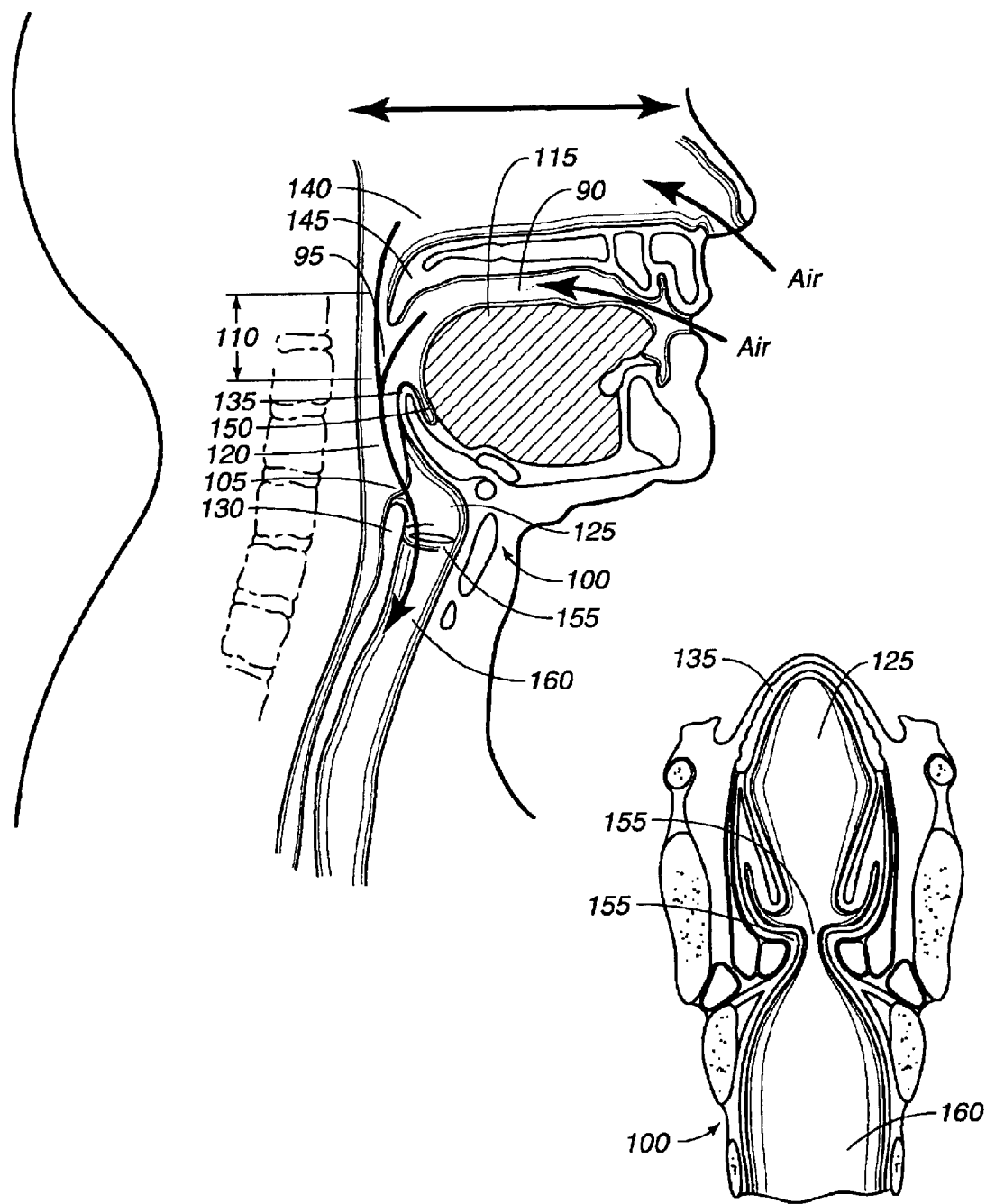
FIG. 5A depicts a sagittal section view of the head and neck along the anteroposterior plane illustrating the anatomy of the upper airway.
FIG. 5B depicts an exploded coronal section view of the larynx.

Referring now collectively to FIGS. 5A–8D, the unique functionality of the instant supraglottic and peri-laryngeal insertion apparatus 10 is clearly demonstrated by examining the anatomical structures of the human upper airway and the methods of maintaining that upper airway with supraglottic airway devices in an anesthetized patient. FIGS. 5A and 5B illustrate the anatomy of the upper airway.

Figure 6A:
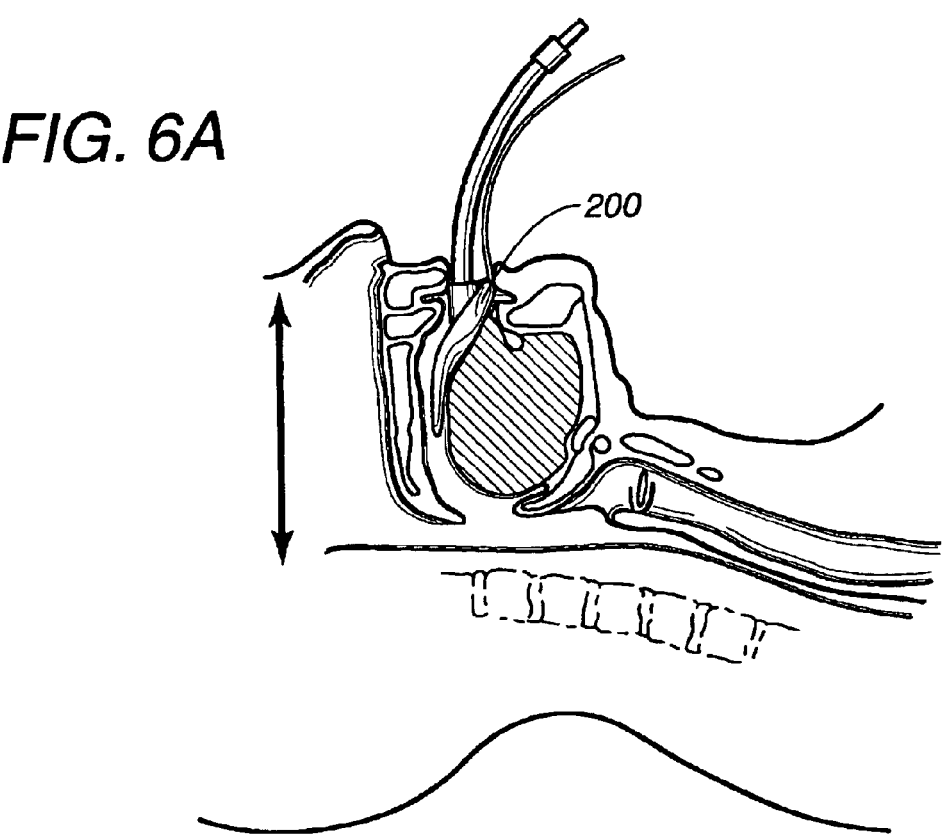
FIG. 6A depicts a sagittal section view of the head and neck illustrating insertion of the LMA supraglottic airway device in the upper airway.
Figure 6B:
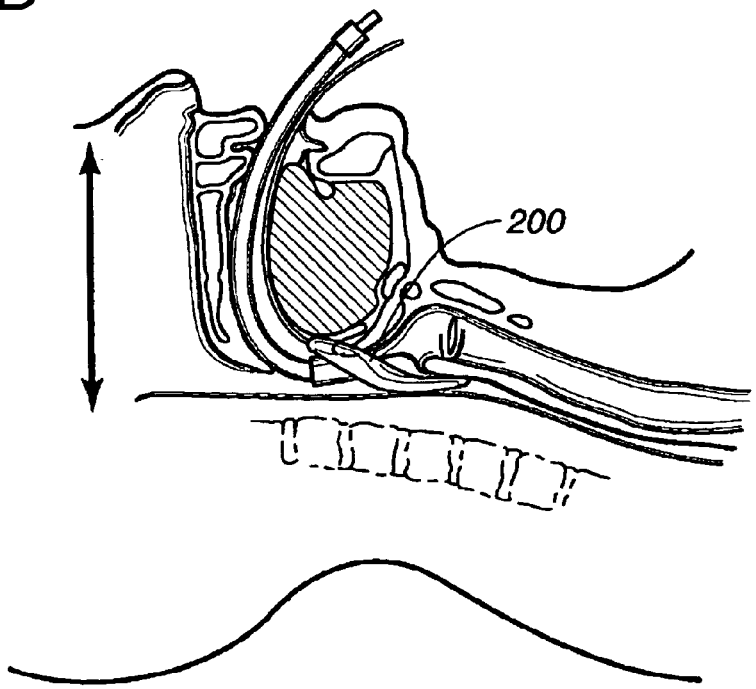
FIG. 6B depicts a sagittal section view of the head and neck illustrating full insertion of the LMA supraglottic airway device in the upper airway.
Figure 6C:
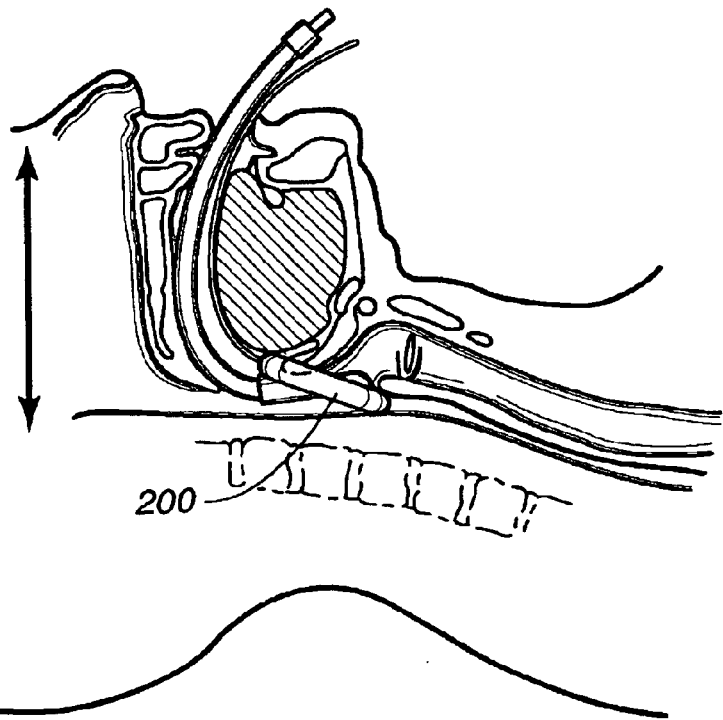
FIG. 6C depicts a sagittal section view of the head and neck illustrating insertion of the COPA supraglottic airway devices in the upper airway.
Figure 6D:
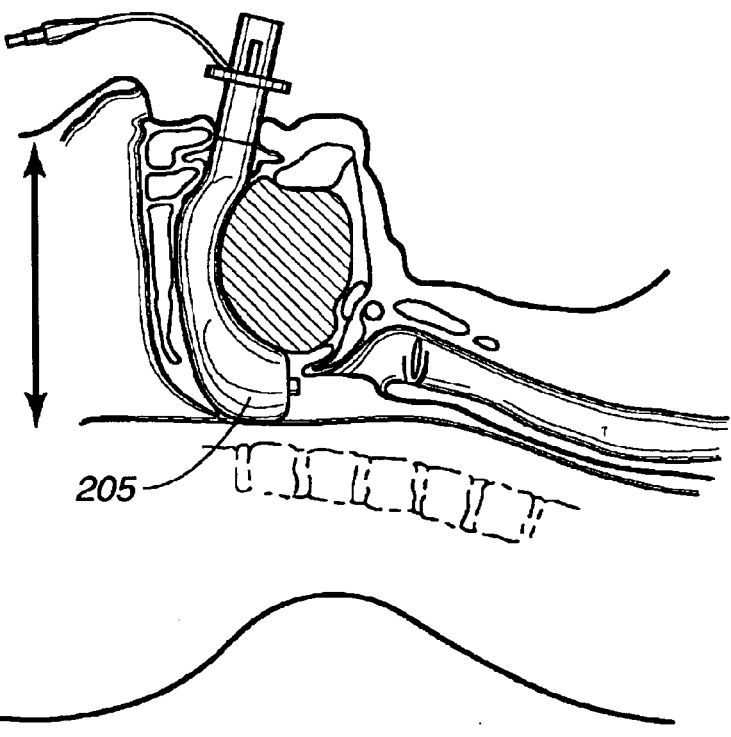
FIG. 6D depicts a sagittal section view of the head and neck illustrating full insertion of the COPA supraglottic airway device in the upper airway.

Turning first to FIG. 5A, with reference to FIGS. 6C and 6D, the sagittal section of the human head and neck along the anteroposterior axis 500, shows the upper human airway with passage of air. The present invention is concerned with that part of the upper airway which extends from the buccal cavity 90, through the pharyngeal cavity 95 to the top of the larynx 100 at the laryngeal inlet 105. During anesthesia, the large inflatable cuff or pliant pad which forms the leading distal ends of the supraglottic airway device and the attached tube must be introduced between the open teeth of the patient and into the buccal cavity 90. As can be seen in FIG. 6C, the cuff of the LMA 200 must be inserted around the bend of the throat 110 at the back of the tongue 115 into the pharynx 120 to seal in the supraglottic region 125 in the hypopharynx 130, above the larynx 100 and around the epiglottis 135. FIG. 6D shows that the COPA 205 has a similar inflatable cuff. Another airway device, the GO2 Airway, seals directly at the rim of the laryngeal inlet 105 at the vocal fold 155. The distal ends of the airway devices must not lodge in the nasopharyngeal vault 140 above the soft palate 145, catch on the tongue 115 or the posterior wall of the pharynx 120, or downfold the epiglottis 135.

As can be seen from FIG. 5A, the large, fleshy tongue 115 becomes an obstacle both in the buccal cavity 90 and in the pharyngeal cavity 95 as it falls backwards towards the pharynx 120 when it falls backwards in an anesthetized patient. Thus clearing the tongue 115 from the buccal 90 and pharyngeal 95 cavities is a major concern in airway control. Raising the epiglottis 135 by applying pressure in the vallecula 150 is also desirable to prevent epiglottic downfolding.

Turning next to FIG. 5B, the exploded coronal section of the larynx 100 depicts the details of the supraglottic region 125. The medical practitioner must carefully navigate the structures of this region to properly insert a supraglottic airway device without having the cuff of the airway device downfold the epiglottis 135. Comparing FIGS. 5A and 5B, it will be clear that the base of the tongue 115 meets the structures of the larynx 100 in this region leaving little room for passage of the cuffs and pads of an airway device.

Figure 5C:
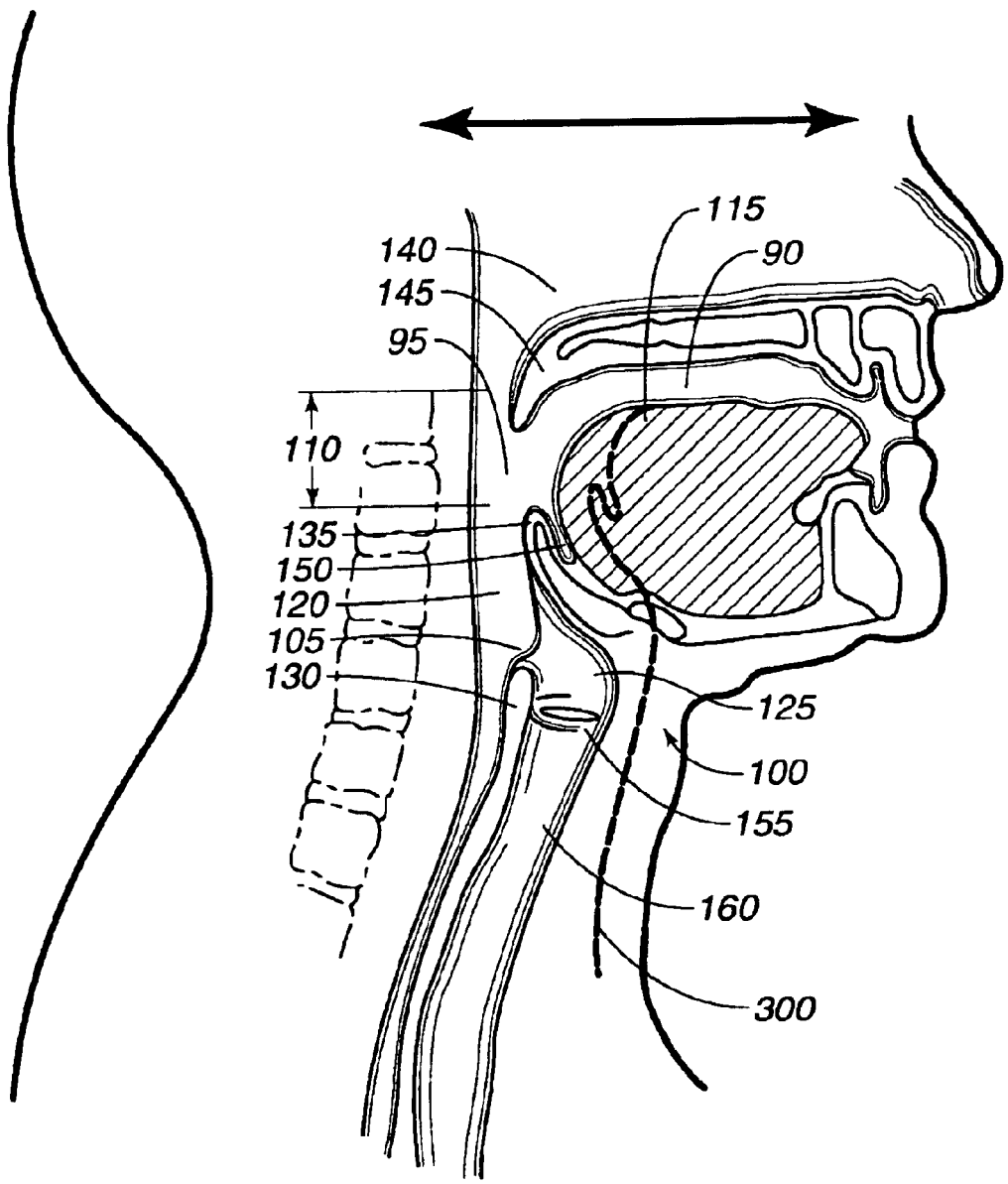
FIG. 5C depicts a sagittal section view of the head and neck illustrating the differences in conformation between the adult and pediatric upper airways.

Referring now to FIG. 5C, the basic conformations of the adult and pediatric airways may be readily compared. It can be seen that the pediatric upper airway 300 is relatively shorter and more anterior than the adult upper airway resulting in a tighter curvature from the buccal cavity 90 into the pharyngeal cavity 95.

Referring now to FIGS. 6A–6D, it is seen how crucial the issue of space becomes when inserting a supraglottic airway device. Space is critical even though the cuffs of airway devices, such as the LMA 200 and the COPA 205, are inserted deflated and are inflated only after proper full insertion of the device is ensured. FIG. 6A shows the LMA cuff 200 introduced into the buccal cavity 90 of the mouth. Thus oriented, the LMA is to pass on down the pharynx 120 to the position illustrated by 6B. FIG. 6C shows the COPA 205 introduced into the mouth with the reverse Guedel technique. From this position, the COPA 205 is rotated 180° as it is advanced into the mouth and pharynx 120 to the final position in the hypopharynx 130, as illustrated by FIG. 6D. Clearly, the tongue 115 is a major obstacle to the passage of these devices around the bend of the throat 110 and through the pharynx 120 and must be compressed in the pharynx 120 and depressed in the buccal cavity 90 to make space for the supraglottic airway device.

Figure 7A:
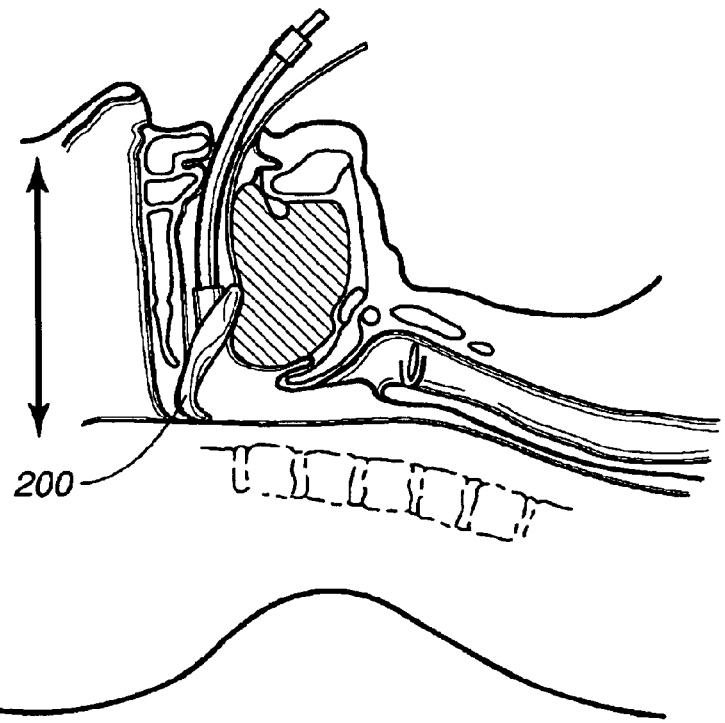
FIG. 7A depicts a sagittal section view of the head and neck illustrating a complication corresponding to impaction of the LMA in the naso-pharyngeal vault during conventional insertion of a supraglottic airway device.
Figure 7B:
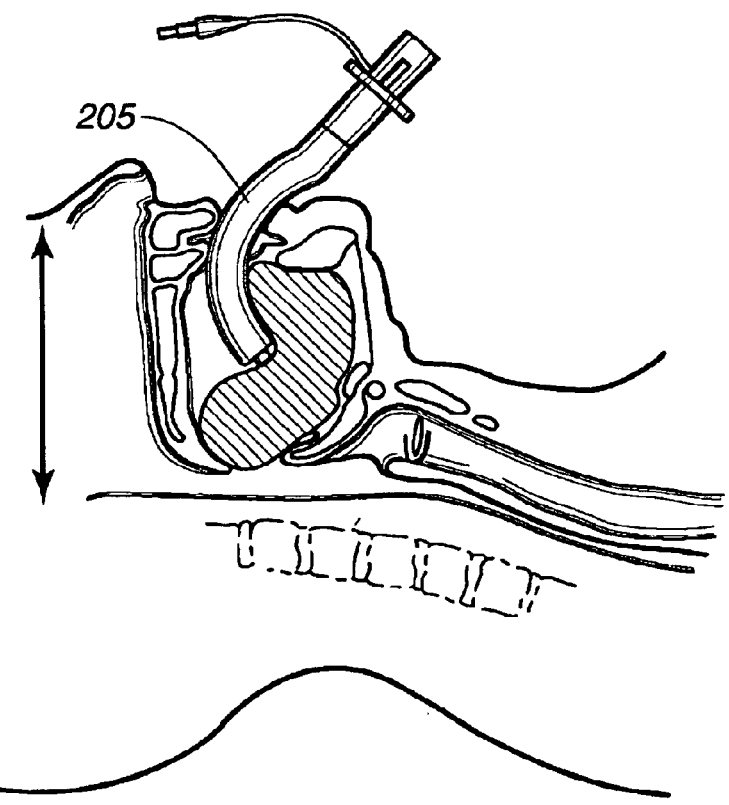
FIG. 7B depicts a sagittal section view of the head and neck illustrating a complication corresponding to bunching of the tongue at the distal end of of the COPA during conventional insertion of a supraglottic airway device.
Figure 7C:
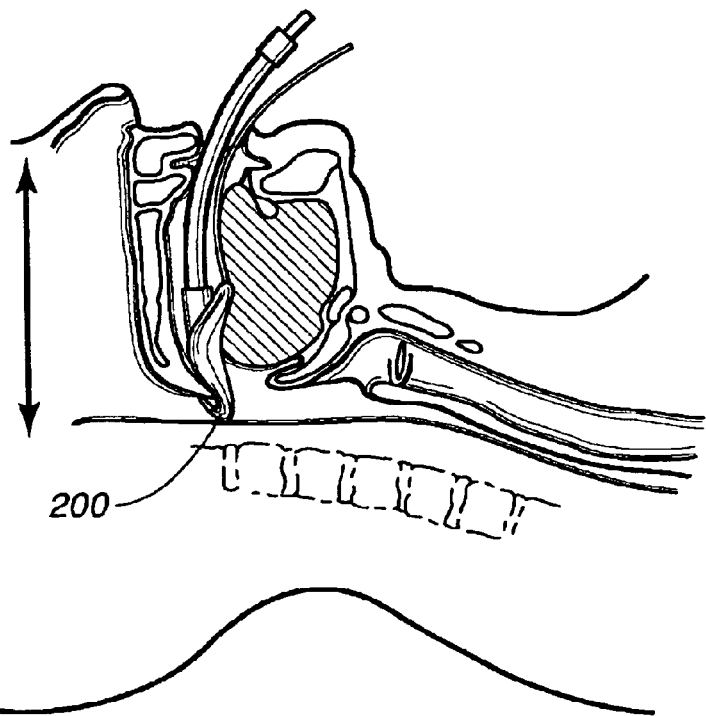
FIG. 7C depicts a sagittal section view of the head and neck illustrating a complication corresponding to backfolding of the LMA cuff at the buccal cavity during conventional insertion of a supraglottic airway device.

FIGS. 7A–7C illustrate some of the common complications which can occur when there is not enough space for a supraglottic airway device to negotiate passage around the surface of the tongue 115. FIG. 7A shows a supraglottic device impacted in the nasopharyngeal vault 140 above the soft palate 145 because the practitioner could not bend the leading device around the bend at the back of the throat 110. FIG. 7B shows how the large, fleshy tongue 115 may catch the airway device and bunch up at the distal tip, obstructing both the device and the pharynx 120. In FIG. 7C, an LMA cuff 200 has negotiated the tongue 115 but has caught on the soft palate 145 or the wall of the pharynx 120 and has folded back upon itself, obstructing the airway and preventing proper inflation of the cuff 200. A backfolded cuff can cause tissue damage or even dislocate cartilage.

Referring now collectively to FIGS. 5A–5B, 6C–6D and 7D, several other potential complications become clear. FIGS. 5A and B illustrate how the epiglottis 135, which lies at the intersection of the laryngeal inlet 105 and the base of the tongue 115, must stand erect for air to pass through the laryngeal inlet 105 and into the trachea 160 below. FIGS. 6B and 6D, show the proper insertion of the LMA 200 and the COPA 205, respectively, at the base of the tongue 115 in the hypopharynx 130 so that the epiglottis 135 stands erect in the bowl of an airway device, maintaining an open airway. Too shallow an insertion of the distal tip of the device allows obstruction of the device by pharyngeal tissues.

Figure 7D:
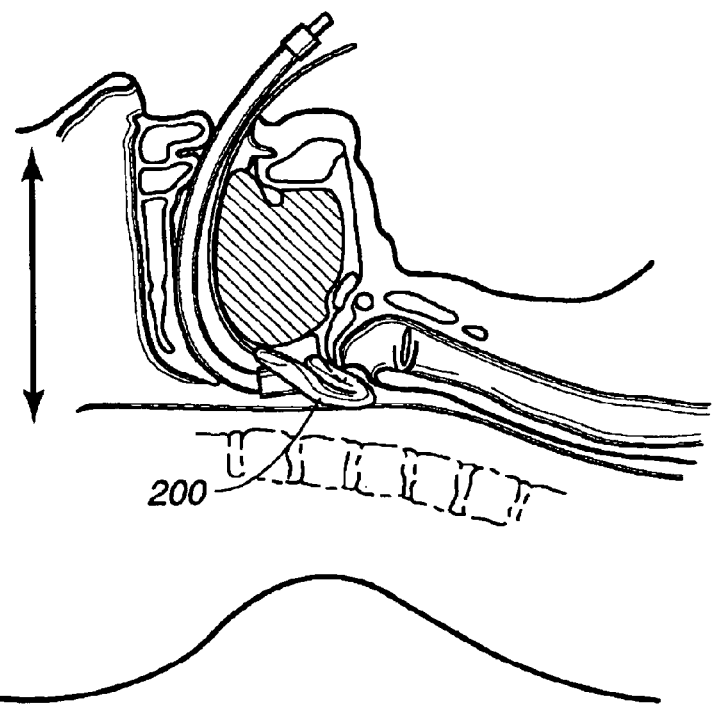
FIG. 7D depicts a sagittal section view of the head and neck illustrating a complication corresponding to an epiglottis downfolded by a LMA cuff with the LMA being fully inserted into the larynx, during conventional insertion of a supraglottic airway device.

Comparing FIGS. 5A and 7D, it may be seen that the epiglottis 135 is vulnerable because it extends out into the narrowing pharyngeal cavity 95. Too deep an insertion of the supraglottic airway device may catch the tip of the epiglottis 135, downfolding the epiglottis 135 and occluding the airway. Alternatively, impingement of the epiglottis 135 may lead to a dangerous laryngospasm. Additionally, even deeper an insertion could push the device past the epiglottis 135 and the distal end could become impacted in the larynx 100. Only once the supraglottic device is fully inserted may the cuff of the device be inflated.

Therefore, insertion of the supraglottic airway devices must be precise. The tongue 115 must be compressed in the pharyngeal cavity 95 and flattened in the buccal cavity 90 to allow adequate space for free, unobstructed insertion of the airway device. Insertion must be neither too shallow or too deep, coming exactly to the base of the tongue 115 in the hypopharynx 130 and having epiglottis 135 erect in the bowl of the cuff 200. To aid insertion, practitioners often feel the need to use their fingers or hands within the buccal cavity 90.

The epiglottis 135 may normally be raised simply by tilting the patient's head but this does not protect against physical impingement. The epiglottis 135 must be upfolded mechanically by applying pressure with a tool placed in the vallecula 150 at the base of the tongue 115. Using the same tool to upfold the epiglottis 135 and to compress, lift and flatten the tongue 115 would be optimal. This is what the present invention does when used by the method described hereinafter.

FIGS. 5A and 8A–8D illustrate the proper use of the superglottic and perilaryngeal insertion apparatus of the present invention. It will be clear to those skilled in the art, that the patient will be in the proper preparatory position for insertion of a supraglottic device, that is, supine, face up, neck flexed and head extended. Referring now to FIG. 5A, the medical practitioner grasps handle member 12 of the insertion apparatus 10, usually with the left hand, so that the compressor-lever shield member 16 faces away from the practitioner parallel to the practitioner's anteroposterior axis 500.

Figure 8A:
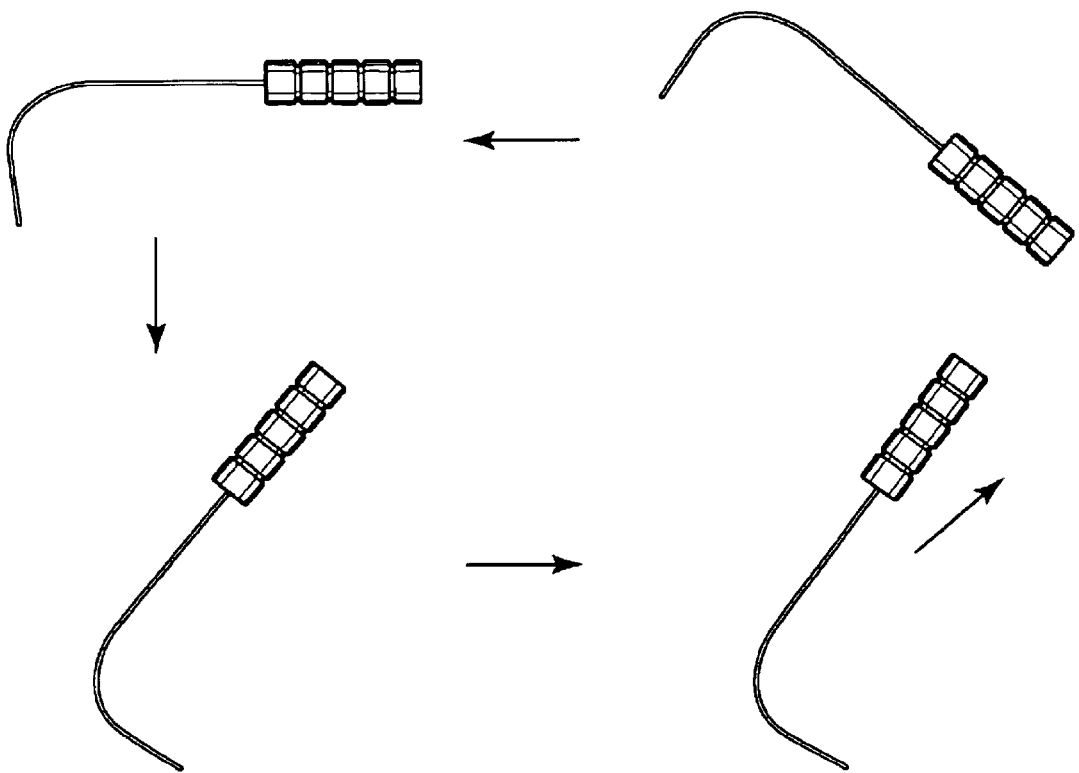
FIG. 8A depicts a cross-section view of the insertion apparatus of the present invention showing the standard technique used in the adult or pediatric airway.

The standard technique contemplated for the use of the present invention in the insertion of supraglottic airway devices in the anesthetized patient will be readily understood by those skilled in the art. As illustrated in FIG. 8A:

Step 1, the practitioner inserts the present invention through the teeth into the open mouth of the patient, in the buccal cavity 90 above the tongue 115. The handle 12 is angled down. The compressor-lever shield 16 is almost vertical above the tongue 115.

Step 2. The practitioner rotates handle member 12 up, rostrally, to advance the distal half of the offset member 14 around the tongue 115.

Step 3. The practitioner continues additional rostral, upwards rotation of the handle 12 to place the distal insertion end 34 of the compressor-lever shield 16 in the vallecula.

Step 4. Finally, the practitioner maintains the angle of the handle 12 while drawing it backwards to apply gentle forward and anterior traction from the base of the tongue 115.

Figure 8B:
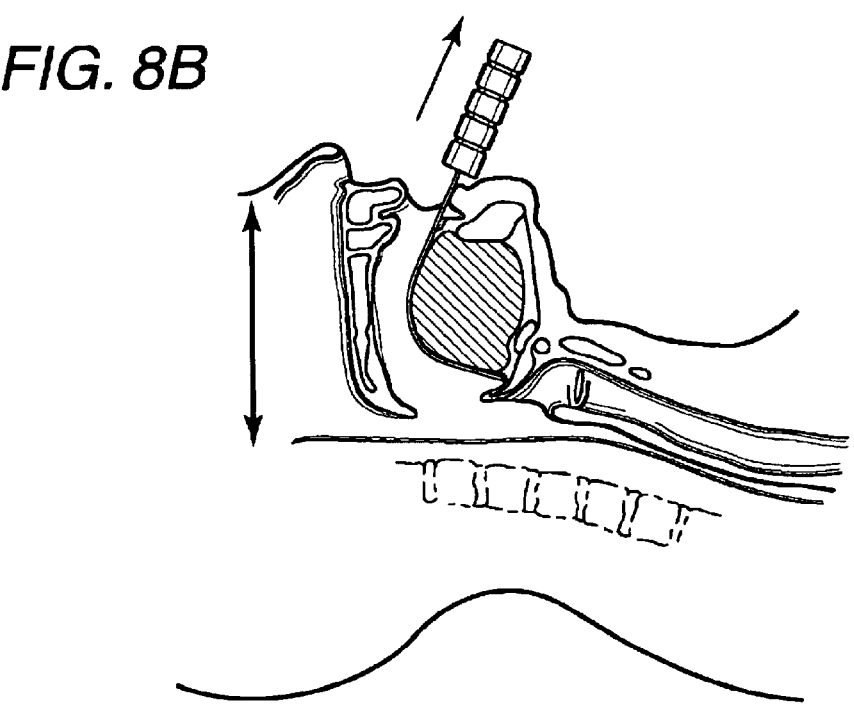
FIG. 8B depicts a sagittal section view of the head and neck illustrating the final position of the insertion apparatus of the present invention disposed in the adult and pediatric upper airway.

As depicted in FIG. 8B, this final step simultaneously compresses and lifts the tongue 115 forward and upfolds the epiglottis 135. While continuing to exert gentle traction on the insertion apparatus 10 of the present invention with one hand, usually the left hand, the practitioner uses the other hand, usually the right hand, to insert the supraglottic airway device posterior to the insertion apparatus 10.

Figure 8C:
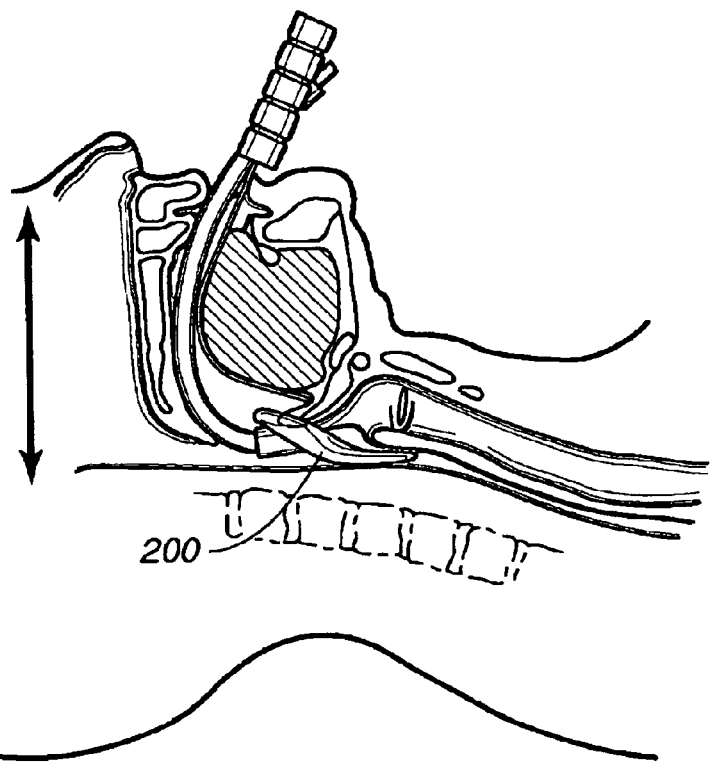
FIG. 8C depicts a sagittal section view of the head and neck illustrating the final position of the insertion apparatus of the present invention with a fully inserted LMA airway device disposed in the adult upper airway.
Figure 8D:
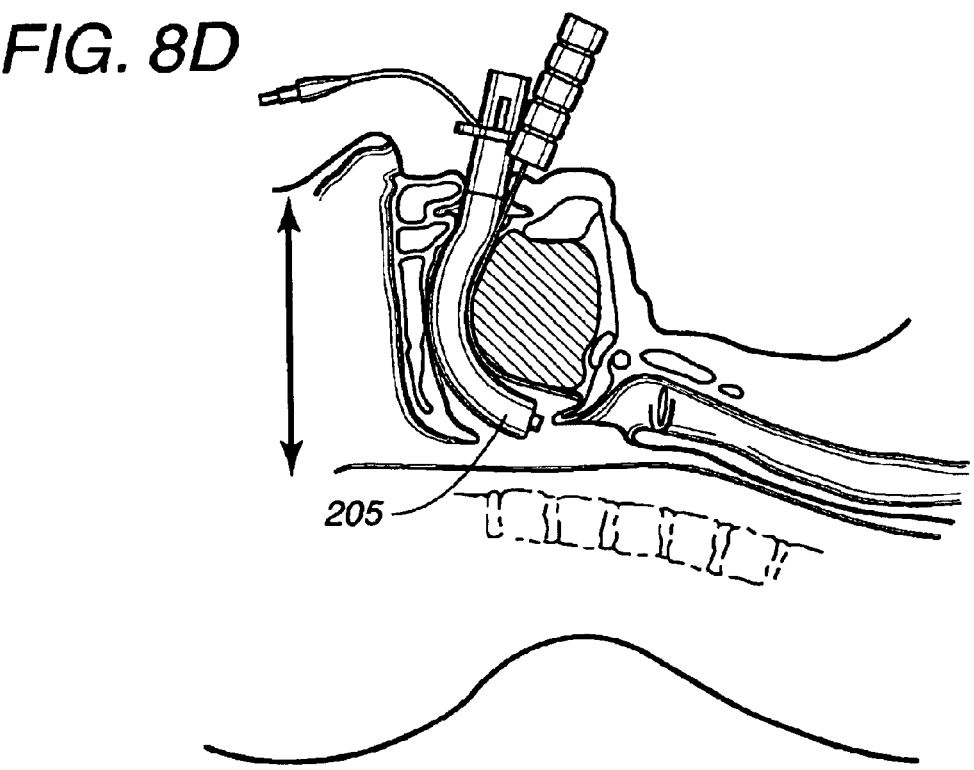
FIG. 8D depicts a sagittal section view of the head and neck illustrating the final position of the insertion apparatus of the present invention with a fully inserted COPA airway device disposed in the adult upper airway.

FIGS. 8C and 8D illustrate the final position of the insertion apparatus 10 anterior to the fully inserted supraglottic airway devices, the LMA 200 and the COPA 205, respectively. Only after successful insertion is the cuff of the airway device inflated.

In an alternative technique, before using the insertion apparatus 10, the practitioner may first introduce the deflated supraglottic airway device into patient's mouth, advancing the distal tip of the device into buccal cavity 90 as far as the soft palate 145. Next the practitioner introduces the insertion apparatus 10 anterior to the airway device, that is between the airway device and the tongue 115. The practitioner then proceeds with Steps 2–4. Having positioned the insertion apparatus 10, the practitioner continues to exert gentle traction and advances the supraglottic airway device into the hypopharynx 130. The cuff 200 of the supraglottic device may then be inflated.

Returning now to FIGS. 5C and 8B for comparison of the pediatric airway 300 with the adult airway, it is clear that a pediatric insertion apparatus 10 and method of use should preferably be similar to the adult apparatus and method. The essential issues of creation of space in the buccal 90 and pharyngeal 95 cavities and protection of the epiglottis 135 remain the same. Epiglottic downfolding is an even greater concern because the more U-shaped epiglottis 135 sits higher in the airway, closer to the soft palate 145, and protrudes out over the laryngeal inlet 105 and lacks tone, making downfolding more likely. The relatively larger tongue 115 and more cephalad position of the larynx 100 and epiglottis 135 combine with the relatively shorter and more anterior pediatric upper airway 300 to require specially designed pediatric series of insertion apparatus 10. The pediatric series should preferably be slightly angulated anteriorly at the distal insertion end 34 to negotiate the vallecula 150.

FIG. 8B illustrates how the pediatric series of the insertion apparatus 10 of the present invention accommodates the tighter curvature of the pediatric airway 300. The practitioner will have to adjust the standard technique of use, applying slightly more rostral rotation to the handle 12 of the insertion apparatus 10 to approximate the vallecula 150 with the distal insertion end 34 of the compressor-lever shield 16.

Having used the insertion apparatus of the present invention to make adequate space in the buccal 90 and pharyngeal 95 cavities and to upfold the epiglottis 135, the practitioner can freely and rapidly insert the airway device without tissue trauma and complications. The practitioner does not need to use fingers or hands within the buccal 90 cavity. The airway device does not become impacted in the nasopharyngeal vault 140 but can pass around the bend of the throat 110 and pass on through the pharyngeal cavity 95. The airway device cannot catch and downfold the tip of the epiglottis 135 and occlude the upper airway. Use of the present invention in this manner increases the space in the pharyngeal cavity 95, enhances access to the laryngeal inlet 105 and ensures an open airway.

It should thus be apparent that the teachings of the present invention improve the manner and means for inserting supraglottic airway devices in an anesthetized patient. No other existing tool can serve all of the functions provided by the insertion apparatus 10.

Forceps are inefficient because pulling the tongue 115 forward does not compress the tongue in the pharyngeal 95 and buccal 90 cavities. Furthermore, the tongue may slip from the grasp of the forceps, requiring multiple forceps-related maneuvers, thus impeding contemporaneous insertion of the airway device. It should be evident that injury to the tongue could occur.

Similarly, conventional straight-blade tongue depressors are used for compression of the tongue during examination of the pharynx of an awake or lightly sedated patient. Straight-blade tongue-depressors can be used to press on the vallecula 150 and mechanically raise the epiglottis 135 but not while depressing the tongue. Such depressors as cannot reach down the surface of the tongue 115, compressing and lifting the tongue 115 from its base.

For example, Nakagawa, U.S. Pat. No. 4,996,976, designed solely for examination purposes, would angle through the pharyngeal cavity 95 if inserted into the supraglottic region 125, thus obstructing the space and impeding insertion of any supraglottic airway device. It could not compress and lift the thick, fleshy, muscular tongue 115.

Osborne, U.S. Pat. No. 412,409, likewise is designed for examination purposes. The Osborne reflector, while curved for the back of the top surface of the tongue 115, is a small plate not adaptable for applying forward and anterior traction from the base of the tongue 115. Neither could Osborne be used to apply pressure to the vallecula 150 to raise the epiglottis 135.

Wunsch, U.S. Pat. No. 3,890,960, is designed for examination of an awake patient without risk of triggering the gag reflex. The two prongs of the Wunsch spatula would be too weak and the curve of the spatula too flat to be used to apply sufficient force across the base of the tongue 115 to compress and coax the tongue 115 out of the pharyngeal cavity 95 or to press on the vallecula 150 to raise the epiglottis 135.

Flam, in U.S. Pat. No. 5,590,643, is primarily an oral intubating airway with a bite block. The attached tongue retractor which is purported to hold part of the tongue 115 forward in the mouth and out of the bend of the throat 110 is specifically short to avoid triggering the gag response. It will be clear to those skilled in the art that Flam could not be used or adapted to quickly compress and lift the tongue out of the pharyngeal cavity. It is too short to press on the vallecula 150 to raise the epiglottis 135.

Anunta, U.S. Pat. No. 6,003,510, is primarily used to leverage an already partially inserted LMA away from the posterior wall of the pharynx 120 so that the cuff 200 does not fold back upon itself. It is inserted posterior to the LMA which is then pushed on down to the hypopharynx 130. The distal tip of Anunta is inserted no farther than the soft palate 145.

Anunta is disclosed as having an optional, ancillary use to compress the tongue solely within the buccal cavity 90 before the LMA is initially introduced above Anunta. Anunta must then be removed and reinserted above the LMA so that Anunta is posterior to the LMA during the remainder of the insertion process. These maneuvers take up time. Additionally, as will be clear to those skilled in the art, the insertion portion of Anunta has too flat a curve to follow the surface of the tongue 115 around the bend into the throat 110 and down the pharynx 120 to the tongue 115-epiglottis 135-vocal fold 155 interface; the insertion end of Anunta would inevitably lodge in the posterior wall of the pharynx 120 near the bend of the throat 110 and stop. Thus, Anunta is designed expressly for use in the buccal cavity 90 and could not be used to clear the upper airway by compressing and lifting the tongue 115 and raising the epiglottis 135.

The laryngoscopic blades used by those skilled in the art to visualize the larynx 120 and mechanically raise the epiglottis 135 for intubation are likewise unadaptable to use for compression and lift of the tongue 115. A laryngoscopic blade merely displaces the tongue 115 to one side.

Schneider, U.S. Pat. No. 5,888,195, provides an adjustable curvature for better visualization of the larynx 100 but is not designed to compress and coax the tongue 115 out of the pharynx 120 or flatten the tongue 115 in the buccal cavity 90. Schneider purports to allow greater control of the tongue 115 by gradually widening the blade towards the top near the handle. and therefore could not compress the width of the base of the tongue 115 as is necessary to coax the tongue 115 up and out of the pharyngeal cavity 95. Furthermore, besides the tongue 115 obtruding around the tip of the blade, the practitioner would find it difficult to place the Schneider tool in the vallecula 150 to raise the epiglottis 135.

Haase, U.S. Pat. No. 5,993,383, discloses a laryngoscopic blade that purports to improve tongue control during intubation, using frustrum-shaped, mirror-image wing sections disposed toward the insertion tip. However, as will be clear to those skilled in the art, these wings merely compress the tongue 115 out of the line of sight, rather than compressing and coaxing the tongue 115 up and out of the pharyngeal cavity 95. The blade itself would be inappropriate for insertion of a supraglottic airway device in a patient because it is configured with a deep channel to guide insertion of the endotracheal tube, thereby consuming space in the pharyngeal cavity 95 and obstructing insertion of a supraglottic airway device.

Other variations and modifications will, of course, become apparent from a consideration of the structures and techniques hereinbefore described and depicted. Accordingly, it should be clearly understood that the present invention is not intended to be limited by the particular features and structures hereinbefore described and depicted in the accompanying drawings, but that the present invention is to be measured by the scope of the appended claims herein.

What is claimed is:

1. A superglottic and peri-laryngeal apparatus for insertion of an airway device from a buccal cavity into a pharyngeal cavity of an upper airway region of a patient, said apparatus comprising:

an offset member having a proximal end and a distal end, a first portion at said proximal end of said offset member, a second portion at said distal end of said offset member, and an arcuate portion between said first portion and said second portion, said first portion having a first given length, said second portion having a second given length, said arcuate portion forming a given angle;

a handle member in attachment to said first portion of said offset member; and a compressor-lever shield member having a proximal end and a distal end, said proximal end of said compressor-level shield member configured to extend from said distal end of said offset member, a third extending from said proximal end to said distal end of said compressor-lever shield, said third portion having a third given length, said second given length of said second portion and said third given length of said third given portion extending a given distance to position said distal end of the compressor-lever shield within a vallecula adjacent to an epiglottis in the pharyngeal cavity with said first portion of said offset member disposed on a dorsal surface of the tongue;

wherein said first given length, said second given length, said third given length, and said given angle of the arcuate portion are configured for simultaneously flattening the tongue in the buccal cavity with the first portion, compressing and lifting the tongue in the pharyngeal cavity with the second portion and the third portion, and mechanically unfolding the epiglottis with the distal end of said compressor-lever shield advanced into the vallecula.

2. The apparatus recited in claim 1, wherein said handle member, said offset member, said arcuate member, and said compressor-lever shield member are integrally constructed.

3. The apparatus recited in claim 1, wherein said handle member and said arcuate offset member are releasably interconnected by a first connection means.

4. The apparatus recited in claim 3, wherein said first connection means comprises a threaded engagement between said handle member and said first portion of said arcuate offset member.

5. The apparatus recited in claim 3, wherein said first connection means comprises a slotted engagement between said handle member and said first portion of said arcuate offset member.

6. The apparatus recited in claim 1, wherein said offset member and said compression-lever shield member are interconnected by a second connection means.

7. The apparatus recited in claim 6, wherein said second connection means comprises a slotted channel engagement between said offset member and said compression-lever shield member.

8. The apparatus recited in claim 1, wherein said compression-lever shield member comprises a substantially flat configuration.

9. The apparatus recited in claim 1, wherein said compression-lever shield member comprises a substantially concave configuration.

10. The apparatus recited in claim 1, wherein said compression-lever shield member comprises a perimeter buffered edge to prevent tissue trauma as said shield member is advanced by said medical practitioner through said patient's pharyngeal cavity into said vallecula.

11. The apparatus recited in claim 1, wherein said arcuate offset member includes a marker means disposed on said proximal end of said offset member, and said marker means configured to indicate when said compressor-level shield member has been fully inserted into said upper airway.

* * * * *